United States Patent
Ophir et al.

(10) Patent No.: US 9,067,035 B2
(45) Date of Patent: *Jun. 30, 2015

(54) DRYING SUBSTANCES, PREPARATION AND USE THEREOF

(75) Inventors: Amos Ophir, Karkur (IE); Eyal Cohen, Kfar-sabba (IE); David Dishon, Pardess Hanna Karkur (IE); Joshua Lewis Colman, Jerusalem (IE)

(73) Assignee: Oridion Medical (1987) Ltd., Jerusalem (IL)

( * ) Notice: Subject to any disclaimer, the term of this patent is extended or adjusted under 35 U.S.C. 154(b) by 719 days.

This patent is subject to a terminal disclaimer.

(21) Appl. No.: 12/379,833

(22) Filed: Mar. 3, 2009

(65) Prior Publication Data

US 2010/0226824 A1 Sep. 9, 2010

(51) Int. Cl.
 *B01D 53/26* (2006.01)
 *A61M 16/08* (2006.01)
 *B01D 69/12* (2006.01)
 (Continued)

(52) U.S. Cl.
 CPC .......... *A61M 16/0875* (2013.01); *A61B 5/0836* (2013.01); *A61M 2230/43* (2013.01); *B01D 61/364* (2013.01); *B01D 69/125* (2013.01); *B01D 2323/38* (2013.01); *C08F 255/00* (2013.01); *C08F 257/02* (2013.01); *C08F 259/08* (2013.01); *C08F 283/06* (2013.01); *C08J 7/123* (2013.01); *C08L 23/02* (2013.01); *C08L 51/003* (2013.01); *C08L 53/025* (2013.01); *B01D 53/228* (2013.01); *B01D 67/0093* (2013.01); *B01D 71/28* (2013.01);
 (Continued)

(58) Field of Classification Search
 CPC .. B01D 53/268; B01D 53/28; B01D 67/0006; B01D 71/34; B01D 69/125; C08F 255/00; C08F 257/02; C08F 259/08; A61M 16/142
 USPC ......... 422/84; 264/232, 129; 427/243; 96/10; 525/291, 326.2, 333.9
 See application file for complete search history.

(56) References Cited

U.S. PATENT DOCUMENTS 3,753,558 A 8/1973 Sheroff
4,670,146 A 6/1987 Inoue
(Continued)

FOREIGN PATENT DOCUMENTS

EP 0381477 B2 8/1990
GB 1351188 4/1974
(Continued)

OTHER PUBLICATIONS

Nasef et al. J. Mem. Sci. 2005, 268, 96-108.*
(Continued)

*Primary Examiner* — Mark Kaucher
(74) *Attorney, Agent, or Firm* — Rodney J. Fuller; Booth Udall Fuller, PLC

(57) ABSTRACT

There is provided herein a dryer polymer substance comprising a polymer grafted with a compound having sulfonic groups, wherein the substance is adapted to pervaporate a fluid such as water, water vapor or both. There is further provided a process for the preparation of a dryer polymer substance adapted to pervaporate a fluid, the process includes processing a polymer into a desired form, activating at least a portion of the polymer, and grafting the activated portion of the polymer with a compound having groups adapted to be sulfonated.

16 Claims, 10 Drawing Sheets

(51) Int. Cl.

| | | |
|---|---|---|
| C08F 255/00 | (2006.01) | |
| C08F 257/02 | (2006.01) | |
| C08F 259/08 | (2006.01) | |
| C08F 283/06 | (2006.01) | |
| C08J 7/12 | (2006.01) | |
| C08L 23/02 | (2006.01) | |
| C08L 51/00 | (2006.01) | |
| C08L 53/02 | (2006.01) | |
| B01D 53/22 | (2006.01) | |
| B01D 67/00 | (2006.01) | |
| B01D 71/28 | (2006.01) | |
| B01D 71/34 | (2006.01) | |
| A61M 16/14 | (2006.01) | |
| B01D 53/28 | (2006.01) | |
| A61B 5/083 | (2006.01) | |
| B01D 61/36 | (2006.01) | |

(52) U.S. Cl.
CPC ............ *B01D 71/34* (2013.01); *A61M 16/085* (2014.02); *A61M 16/142* (2014.02); *B01D 53/28* (2013.01)

(56) References Cited

U.S. PATENT DOCUMENTS

| | | | | |
|---|---|---|---|---|
| 4,704,324 | A | 11/1987 | Davis | |
| 4,705,543 | A | 11/1987 | Kertzman | |
| 4,755,299 | A | 7/1988 | Bruschke | |
| 4,802,988 | A | 2/1989 | Bartels | |
| 4,808,201 | A * | 2/1989 | Kertzman | 96/10 |
| 4,844,719 | A | 7/1989 | Toyomoto | |
| 5,160,511 | A | 11/1992 | Lovelock | |
| 5,334,314 | A | 8/1994 | Neel | |
| 5,334,341 | A | 8/1994 | Streicher | |
| 5,387,378 | A * | 2/1995 | Pintauro et al. | 264/48 |
| 5,501,212 | A | 3/1996 | Psaros | |
| 6,051,343 | A * | 4/2000 | Suzuki et al. | 429/316 |
| 6,413,298 | B1 * | 7/2002 | Wnek et al. | 95/52 |
| 6,444,343 | B1 * | 9/2002 | Prakash et al. | 429/493 |
| 6,616,842 | B1 | 9/2003 | Soria | |
| 6,635,104 | B2 | 10/2003 | Komkova | |
| 6,779,522 | B2 | 8/2004 | Smith | |
| 7,597,733 | B2 | 10/2009 | Fudge | |
| 2004/0150827 | A1 * | 8/2004 | Potyrailo et al. | 356/432 |
| 2005/0011826 | A1 | 1/2005 | Childs | |
| 2005/0118372 | A1 * | 6/2005 | Bonnet et al. | 428/35.7 |
| 2005/0121317 | A1 * | 6/2005 | Klocke et al. | 204/252 |
| 2006/0000778 | A1 | 1/2006 | Childs | |
| 2006/0021615 | A1 | 2/2006 | Kertzman | |
| 2006/0138044 | A1 | 6/2006 | Krause | |
| 2006/0269815 | A1 | 11/2006 | Goldbach | |
| 2007/0214962 | A1 | 9/2007 | Kozak | |
| 2007/0224480 | A1 | 9/2007 | Yoshida | |
| 2010/0224066 | A1 | 9/2010 | Ophir | |
| 2010/0226823 | A1 | 9/2010 | Rakhman | |

FOREIGN PATENT DOCUMENTS

| | | | |
|---|---|---|---|
| GB | 1380484 B2 | 1/1975 | |
| JP | 03278826 | 12/1991 | |
| WO | 2004/026929 | 4/2004 | |
| WO | 2004/033062 | 4/2004 | |
| WO | WO 2007020640 A2 * | 2/2007 | ............ A61B 5/097 |

OTHER PUBLICATIONS

Huang, R. Y. M. et al., "Dehydration of Isopropanol by Pervaporation Using Aromatic Polyetherimide Membranes," Sep. Sci. Tech., 28(11-12):2035-2048 (1993).

Krasemann, L. et al., "Self-assembled polyelectrolyte multilayer membranes with highly improved pervaporation separation of ethanol/water mixtures," J. Membr. Sci., 181(2):221-228 (2001).

Krasemann, L. et al., "Ultrathin self-assembled polyelectrolyte membranes for pervaporation," J. Membr. Sci., 150 (1):23-30 (1998).

Meier-Haack, J. et al., "Pervaporation separation of water/alcohol mixtures using composite membranes based on polyelectrolyte multilayer assemblies," J. Membr. Sci., 184(2)233-243 (2001).

Yamasaki, A. et al., "Effect of Evaporation Time on the Pervaporation Characteristics through Homogeneous Aromatic Polyamide Membranes. II. Pervaporation Performances for Ethanol/Water Mixture," J. Appl. Polym. Sci., 60 (5):743-748 (1996).

IHM, Chang-Do and IHM, Son Ki, "Pervaporation of water-ethanol mixtures through sulfonated polystyrene membranes prepared by plasma graft-polymerization", J Membr Sci, 98(1-2):89-96 (1995).

Mika, A. M. et al., "A new class of polyelectrolyte-filled microfiltration membranes with environmentally controlled porosity", J Membr Sci 108(1):37-56 (1995).

David, M. O. et al., "Pervaporation membranes endowed with catalytic properties, based on polymer blends. Journal of Membrane", Science, 73(2):129-141 (1992).

Scherer, Gunter G., "Polymer membranes for fuel cells", Berichte Der Bunsen-Gesellschaft Fur Physikalische Chemie Verlag Chemie, 94:(9):1008-1014 (1990).

U.S. Appl. No. 12/379,829 Non-Final Rejection Jun. 13, 2011.

U.S. Appl. No. 12/379,829 Final Rejection Feb. 8, 2012.

U.S. Appl. No. 12/379,828 Requirement for Restriction/Election Sep. 29, 2011.

U.S. Appl. No. 12/379,828 Non-Final Rejection Dec. 15, 2011.

U.S. Appl. No. 12/379,828 Final Rejection Jul. 11, 2012.

* cited by examiner

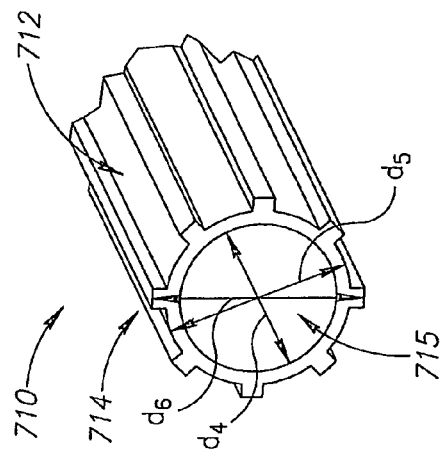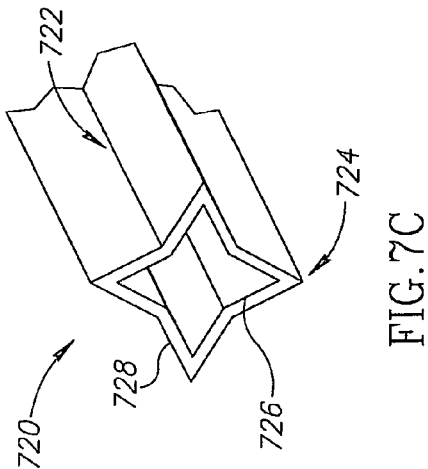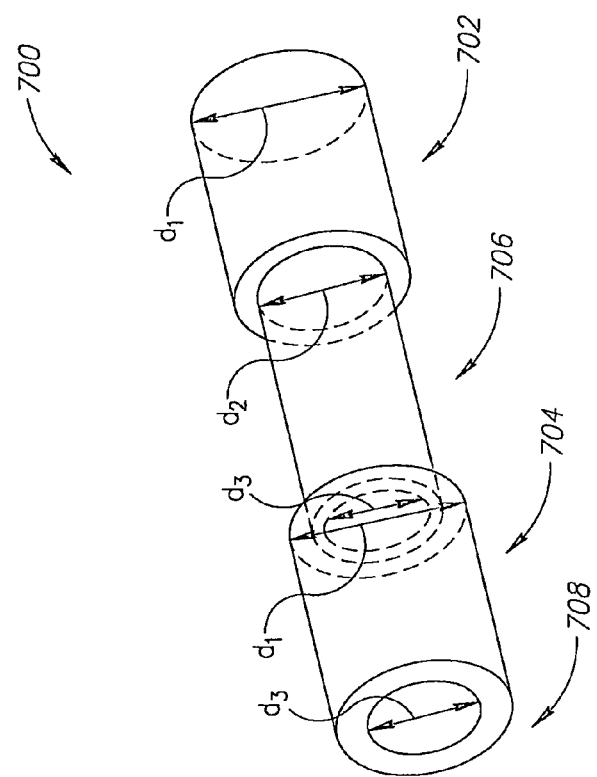

DRYING SUBSTANCES, PREPARATION AND USE THEREOF

RELATED APPLICATIONS

Cross-reference is made to commonly-owned, copending application Ser. No. 12/379,828 and Ser. No. 12/379,829, filed on even date herewith.

FIELD

The invention relates to the field of membranes and other substrates exhibiting water pervaporation properties.

BACKGROUND

The separation or removal of liquids, such as water, from gases, such as organic gases, is an important process within the chemical, petrochemical, medical and energy industries. Water removal is important in the primary production of a wide range of organic solvents, in the recovery and recycling of used solvents, and in the removal of water from chemical equilibrium reactions to drive the reaction towards a preferred product.

Another application that requires gas that is free or essentially free of liquids, such as water, is medical breath analysis, which is performed to provide information related to a patient's condition. An example of a gas analysis often performed is capnography, which is the monitoring of respiratory carbon dioxide ($CO_2$) concentration, usually time dependent. The time dependent respiratory $CO_2$ concentration may be used to directly monitor the inhaled and exhaled concentration of $CO_2$, and indirectly monitor the $CO_2$ concentration in a patient's blood. Other gases such as oxygen ($O_2$), carbon monoxide (CO), nitrogen or the like may also be measured individually or in combination.

In breath analysis systems, for example capnography, breath gas can be sampled such as by a mainstream or a sidestream analyzer. In mainstream analyzers, the sample chamber is positioned within the patient's gas stream, usually near the patient's end of the breathing system. This arrangement is normally heavier and more cumbersome than sidestream systems.

In sidestream analyzers, gas is often drawn from the breathing system by a tube. The tube, which may be connected to an adaptor, delivers the gas to a sampling place (such as a sampling chamber). It is preferable that the sampling line is clear of liquids, such as condensed out liquids, in the fluid sample at all times, in order to permit continuous, non-interfered monitoring.

Condensed out liquids generally refer to water that condenses out from the humidity (the water vapor in breath) in the sampling tubes. Condensed out liquids are a major problem commonly hindering breath analyses, particularly sidestream capnography. The internal humidity levels in the tubes are high, especially in proximity to the breath collection area, since the exhaled and inhaled breath is humid and relatively warm. This is also the case in intubated patients who are generally artificially ventilated with gas (for example, air) having up to 100% humidity at a temperature normally above ambient temperature (for example, about 34° C.), depending on the airway humidification system and patient needs. The humidity (water vapors) often condenses on the inside of the tube, particularly as the tube extends farther from the breath collection area due to the temperature decreases.

Various processes that have been used to dehydrate fluids include newer membrane-based techniques such as pervaporation and vapor permeation. Pervaporation is a process that involves a membrane in contact with a fluid (which may include gas and/or liquid) on a feed or upstream side and a vapor on the permeate or downstream side. Usually, a vacuum or an inert gas is applied on the vapor side of the membrane to provide a driving force for the process. Typically, the downstream pressure is lower than the saturation pressure of the permeate. Vapor permeation is quite similar to pervaporation, except that a vapor is contacted on the feed side of the membrane instead of a liquid. As membranes suitable for pervaporation separations are typically also suitable for vapor permeation separations, use of the term "pervaporation" herein encompasses both "pervaporation" and "vapor permeation".

A variety of different types of membranes have been described for use in pervaporation dehydration processes. The materials used to prepare the membranes include hydrophilic organic polymers such as polyvinylalcohol, polyinides, polyamides, and polyelectrolytes. In addition, inorganic materials such as molecular sieves and minerals (for example, zeolites which are aluminosilicate minerals) having a microporous structure have been used.

Initially, polymer-based pervaporation membranes comprised dense, homogeneous membranes. Typical examples of such membranes are described by Yamasaki et al. [J. Appl. Polym. Sci. 60 (1996) 743-48], which is incorporated herein by reference in its entirety. These membranes suffer from low fluxes (amount of fluid that flows through a unit membrane area per unit time) as they are fairly thick. While the flux of the membranes can be increased by decreasing the thickness of the membranes, this leads to a decrease in mechanical strength and robustness.

Two routes have commonly been used to overcome the problem encountered by the above membranes (some of which may be considered homogeneous membranes). The first route involves the use of an asymmetric membrane in which a dense surface layer is supported on a more porous material made from the same polymer. A typical example of such an asymmetric membrane is disclosed by Huang et al. [Sep. Sci. Tech. 28 (1993) 2035-48], which is incorporated herein by reference in its entirety.

A second route involves the formation of a dense thin film on the surface of a suitable support membrane, wherein the chemical composition of the dense surface layer and the supporting membrane are typically different. Typically, the support membrane is an ultrafiltration membrane that may contain an incorporated fabric to provide additional strength. Examples of these thin film composite membranes are described in U.S. Pat. Nos. 4,755,299, 5,334,314, 4,802,988 and EP 0,381,477. One major disadvantage of these thin-film composite membranes, however, is their fragility. For example, the commonly used cross-linked poly(vinylalcohol) films supported on polyacrylonitrile ultrafiltration membrane supports are readily damaged through the formation of cracks in the films and through parts of the film falling away from the support. Great care must therefore be taken when mounting and using these membranes. It is also difficult to prepare such membranes in such a way that they are free of defects.

A special form of the thin-film composite membranes is referred to as a "Simplex" membrane. These are made up of thin films using alternating layers of oppositely charged polyelectrolytes. The membranes are made by successive immersions in solutions of the two different polyelectrolytes such that a multilayer complex is formed (see for example Krasemann et al. [J. Membr. Sci. 150 (1998) 23-30]; Krasemann et al. [J. Membr. Sci. 181 (2001) 221-8], and Haack et al. [J. Membr. Sci. 184 (2001) 233-43]), which are incorporated herein by reference in their entirety. While a high selectivity and reasonable fluxes can be achieved with the Simplex membranes, these membranes are complex to prepare, as they require multiple coating steps. In order to get ideal performance, up to 60 dipping operations are sometimes needed. Another significant drawback lies in the fact that these membranes cannot tolerate feed water contents higher than 25% without loss of some of the multiple layers.

Nafion® Membrane

A conventionally used way for dehydration of gases by pervaporation is using proton conducting membranes, such as the membranes used in proton exchange membrane fuel cells. These membranes, an example of which is sold under the brand name Nafion® by DuPont, are made of a perfluorinated sulfonic acid polymer. Nafion® membranes, which are fully fluorinated polymers, have high chemical and thermal stability and are stable against chemical attack in strong bases, strong oxidizing and reducing acids, $H_2O_2$, Cl, $H_2$ and $O_2$ at temperatures up to about 100° C. Nafion® consists of a fluoropolymer backbone upon which sulfonic acid groups are chemically bonded. However, although usually providing sufficient performance, Nafion® is an expensive material which renders it economically unattractive in most applications.

Nafion® tubes have been used for breath analysis applications (such as capnography), which, as discussed above, require an essentially liquid-free sampled gas. Nafion® tubes include, an inner tube coaxially fitted within the lumen of an outer tube. The inner tube, which is fabricated from a perfluorinated polymer, has a predetermined small internal diameter consistent with breath-by-breath response times. The Nafion® plastic employed exhibits high permeability to moisture (water vapor) but does not readily pass other respiratory gases, such as oxygen and carbon dioxide.

When used in breath analysis, Nafion® is a part of the patient's airway and breath sampling system and thus cannot be transferred from one patient to another and cannot even be re-used for the same patient. This disposable nature of Nafion® increases the cost factor. The cost becomes even more significant in applications that require relatively long Nafion® tubes. For example, when sampling at 150 ml(milliliter)/minute (which is a common flow in capnography, for example), 6 inches of Nafion® are required. This length of Nafion® may cost at least an order of magnitude more than the whole tubing system (such as a breath sampling system)

Because the Nafion® tubing in many applications has very thin walls (typically 0.002-0.003 inch), water permeates through it quickly. The thin walls, however, also dictate a use of secondary structural supports to prevent collapse of the walls. These structural supports complicate the manufacture of the product and also reduce the water permeation.

The Nafion® tubing is fabricated by a process known as blown-film extrusion. This process involves the following steps, which are akin to making trash bags, a material that has walls that are also far too thin to support their own weight. Typical trash bags have a wall thickness of 0.002 or 0.003 inch (hefty trash bags may be a bit thicker). A typical Nafion® medical gas "line" tube is typically 0.0025 inch in wall thickness. And just as a trashcan holds the trash bag open, a mesh insert or an outer sleeve should be used to hold the tubing open from the inside or from the outside, respectively. The mesh may be sufficiently coarsely woven so that it allows circulation of gases to the surface of the tubing; however, as mentioned above, the presence of the mesh insert inside or outside the tube may interfere with the efficiency of the pervaporation process, typically reducing the water pervaporation efficiency by over 50%. Another disadvantage of the Nafion® is the chemically aggressive nature of the raw materials used for its preparation and the difficulty in the processing of these materials. For example, special extrusion means are required in order to allow processing of the Nafion®. Further, integrating Nafion® into tubing systems (such as breath sampling systems) is complicated and require special means.

There is thus a need for membranes and other substrates exhibiting water pervaporation properties, which are effective, easy to handle and manufacture and cost efficient.

SUMMARY

The following embodiments and aspects thereof are described and illustrated in conjunction with systems, tools and methods, which are meant to be exemplary and illustrative, not limiting in scope. In various embodiments, one or more of the above-described problems have been reduced or eliminated, while other embodiments are directed to other advantages or improvements.

According to some embodiments, the present invention provides a robust, high-performance substance (such as a membrane or tube) designed for the selective removal of a polar fluid, such as water, from less polar gases, such as air and $CO_2$, by a pervaporation process.

According to some embodiments, there is provided a dryer polymer substance including a polymer grafted with a compound having sulfonic groups, wherein the substance is adapted to pervaporate a fluid. The fluid may include water, water vapor or both.

According to some embodiments, there is provided a breath sampling system, the system includes a dryer polymer tube including a polymer grafted with a compound having sulfonic groups, wherein the tube is adapted to pervaporate a fluid; and at least one of: a connector adapted to connect the dryer polymer tube to a breath sampling tube and a reinforcement element. The connector, the reinforcement element, or both, may be molded with the dryer polymer tube.

According to some embodiments, the polymer may include a polyolefin, a fluoro-polymer or a combination thereof. The fluoro-polymer may include poly(vinylidene fluoride) (PVDF) or any derivative thereof. The compound having sulfonic groups may include sulfonated styrene, sulfonated polystyrene, sulfonated styrene copolymer or any derivative thereof. The dryer polymer substance may include poly(vinylidene fluoride)-graft-poly(styrene sulfonated acid (PVDF-g-PSSA) or any salt or derivative thereof. The percentage of grafting of the polymer prior to sulfonation polymer may be in the range of 20-50%. The percentage of sulfonation of the dryer polymer substance may be in the range of 40-100%.

According to some embodiments, the dryer tube may have a water uptake of over 100% at a temperature of 22° C. and at 34% humidity, wherein the internal diameter of the tube is 1.0±0.1 millimeter (mm); the outer diameter of the tube is 1.24±0.02 mm and the length of the tube is 50 mm. According to some embodiments, the dryer tube may have a water evaporation rate of over 150 micro-liter/hour at a temperature of 22° C. and at 34% humidity, wherein the internal diameter of the tube is 1.0±0.1 millimeter (mm); the outer diameter of the tube is 1.24±0.02 mm and the length of the tube is 50 mm. According to some embodiments, the dryer tube may have a water evaporation rate of over 250 micro-liter/hour at a temperature of 22° C. and at 34% humidity, wherein the internal diameter of the tube is 1.0±0.1 millimeter (mm); the outer diameter of the tube is 1.24±0.02 mm and the length of the tube is 50 mm.

According to some embodiments, the dryer polymer substance may include a membrane. According to some embodiments, the dryer polymer substance may include dryer tube. The dryer tube may have an essentially circular internal cross-section. The dryer tube may have an essentially circular internal cross-section and a non-circular external cross-section. The dryer tube may have a non-circular internal cross-section and a matching non-circular external cross-section.

The dryer tube may have a non-circular internal cross-section and a matching non-circular external cross-section.

According to some embodiments, the dryer polymer substance may include a dryer tube, wherein the dryer tube may include an inner conduit, wherein the internal cross-section of at least a portion of the inner conduit is essentially non-circular and adapted to collect liquids in proximity to the inner walls of the inner conduit and thus allow an essentially free of liquids flow in the dryer tube. The cross-section of the inner conduit may be essentially similar to an n-point star, wherein n is an integer having the value of between 2-10. The cross-section of the inner conduit may be essentially similar to an n-petal flower, wherein n is an integer having the value of between 2-10.

According to some embodiments, the dryer polymer substance may have an ultimate tensile strength of about 20 MPa or more. The dryer polymer substance may have Young's modulus of about 150 MPa or more. The dryer polymer substance may exhibit ultimate elongation of 80% or more.

According to some embodiments, there is provided a process for the preparation of a dryer polymer substance adapted to pervaporate a fluid, the process includes processing a polymer into a desired form, activating at least a portion of the polymer, and grafting the activated portion of the polymer with a compound having groups adapted to be sulfonated.

According to some embodiments, the groups adapted to be sulfonated may include styrene, polystyrene, styrene copolymer or any derivative thereof.

According to some embodiments, the process may further include sulfonating the groups of the grafted polymer, thereby obtaining a polymer substance adapted to pervaporate water. The percentage of sulfonation of the dryer polymer substance may be in the range 40-100%.

According to some embodiments, the activation may include irradiation, for example, gamma irradiation or any other type of irradiation.

According to some embodiments, processing may include extruding, molding or both. The desired form may include a tube and the resulting dryer polymer substance may include a dryer tube. The dryer tube may have an essentially circular internal cross-section. The dryer tube may have an essentially circular internal cross-section and a non-circular external cross-section. The dryer tube may have a non-circular internal cross-section and a matching non-circular external cross-section. The dryer tube may have a non-circular internal cross-section and a matching non-circular external cross-section.

According to some embodiments, the dryer polymer substance may include a dryer tube, wherein the dryer tube may include an inner conduit, wherein the internal cross-section of at least a portion of the inner conduit is essentially non-circular and adapted to collect liquids in proximity to the inner walls of the inner conduit and thus allow an essentially free of liquids flow in the dryer tube. The cross-section of the inner conduit may be essentially similar to an n-point star, wherein n is an integer having the value of between 2-10. The cross-section of the inner conduit may be essentially similar to an n-petal flower, wherein n is an integer having the value of between 2-10.

According to some embodiments, the polymer may include a polyolefin, a fluoro-polymer or a combination thereof. The fluoro-polymer may include poly(vinylidene fluoride) (PVDF) or any derivative thereof. The compound having sulfonic groups may include sulfonated styrene, sulfonated polystyrene, sulfonated styrene copolymer or any derivative thereof. The dryer polymer substance may include poly(vinylidene fluoride)-graft-poly(styrene sulfonated acid (PVDF-g-PSSA) or any salt or derivative thereof. The percentage of grafting of the polymer prior to sulfonation polymer may be in the range of 20-50%. The percentage of sulfonation of the dryer polymer substance maybe in the range of 40-100%.

According to some embodiments, the dryer tube may have a water uptake of over 100% at a temperature of 22° C. and at 34% humidity, wherein the internal diameter of the tube is 1.0±0.1 millimeter (mm); the outer diameter of the tube is 1.24±0.02 mm and the length of the tube is 50 mm. According to some embodiments, the dryer tube may have a water evaporation rate of over 150 micro-liter/hour at a temperature of 22° C. and at 34% humidity, wherein the internal diameter of the tube is 1.0±0.1 millimeter (mm); the outer diameter of the tube is 1.24±0.02 mm and the length of the tube is 50 mm. According to some embodiments, the dryer tube may have a water evaporation rate of over 250 micro-liter/hour at a temperature of 22° C. and at 34% humidity, wherein the internal diameter of the tube is 1.0±0.1 millimeter (mm); the outer diameter of the tube is 1.24±0.02 mm and the length of the tube is 50 mm.

According to some embodiments, the dryer polymer substance may have an ultimate tensile strength of about 20 MPa or more. The dryer polymer substance may have Young's modulus of about 150 MPa or more. The dryer polymer substance may exhibit ultimate elongation of 80% or more.

According to some embodiments, there is provided a method for the preparation of a tubing system adapted for water pervaporation, the method includes molding a polymer into a form of a tube having at least one connector adapted to connect to one or more additional tubes, at least one reinforcement element or a combination thereof, activating at least a portion of the tube, and grafting the activated portion of the tube with a compound having groups adapted to be sulfonated. The method may further include sulfonating the groups adapted to be sulfonated, thereby obtaining a tubing system including a tube adapted to pervaporate water and at least one connector adapted to connect to one or more additional tubes and/or at least one reinforcement element.

In addition to the exemplary aspects and embodiments described above, further aspects and embodiments will become apparent by reference to the figures and by study of the following detailed descriptions.

BRIEF DESCRIPTION OF THE FIGURES

FIGS. 7a-d show exemplary dryer tubes, according to some embodiments;

DETAILED DESCRIPTION

Figure 1:
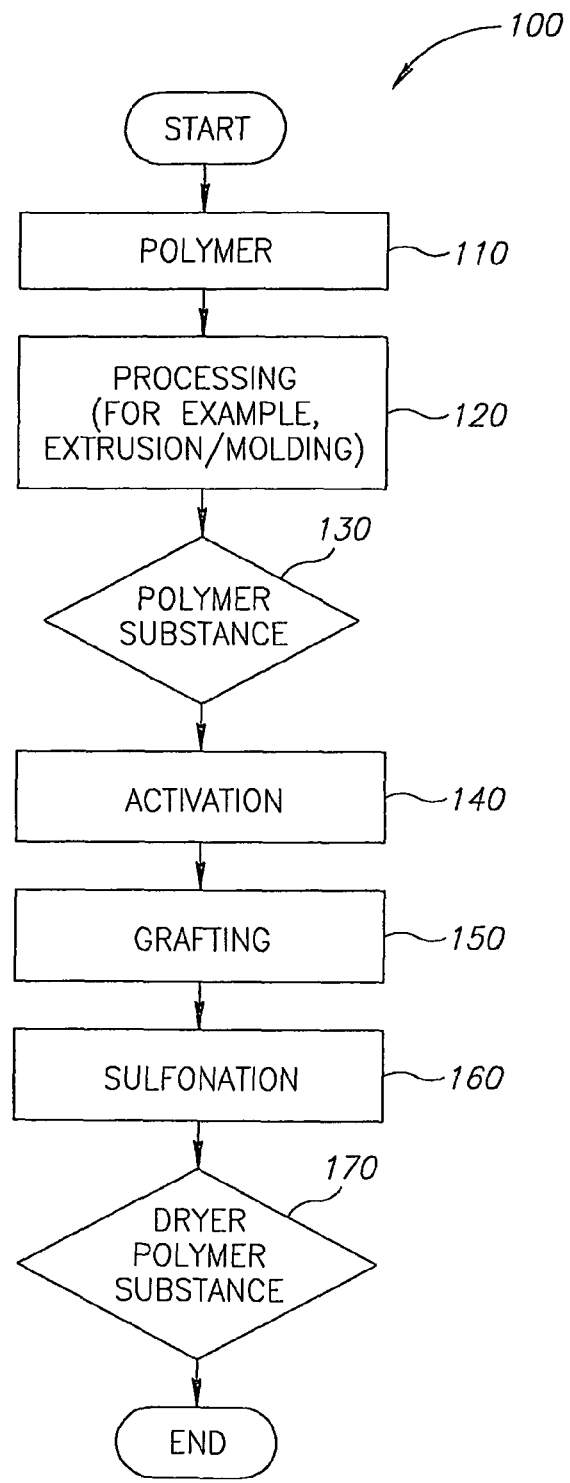
FIG. 1 shows a flowchart describing a general process of production of a dryer polymer substance, according to some embodiments.

In the following description, various aspects of the invention will be described. For the purpose of explanation, specific configurations and details are set forth in order to provide a thorough understanding of the invention. However, it will also be apparent to one skilled in the art that the invention may be practiced without specific details being presented herein. Furthermore, well-known features may be omitted or simplified in order not to obscure the invention.

According to some embodiments of the invention, there is provided a polymer substance, such as, but not limited to, a membrane or a tube, (such as a micro-tube) adapted to dry a gas (such as air, oxygen ($O_2$), oxygenated air, carbon monoxide (CO), carbon dioxide, ($CO_2$) or any other gas) from fluids, such as polar fluids, for example, water and/or water vapors. The polymer substance may further be adapted to allow flow of the gas (along the membrane or through the tube), while essentially maintaining the concentrations of other gas components (such as carbon dioxide, $CO_2$, oxygen, nitrogen or any other gas).

The polymer substance may be adapted to be incorporated in sampling and/or analyzing systems, such as in a breath test analysis system. In breath test analysis, (particularly in side stream breath test analysis) exhaled breath is sampled from a subject and passed through a tubing system to an analyzer which provides information regarding the composition of the gas sample and/or characteristics and/or behavior of any of the gas components (for example $CO_2$). In order to obtain accurate analysis of the exhaled gas, the breath sample should maintain the initial composition and characteristics of certain components but should also be essentially free of water. The polymer substance, according to some embodiments of the invention, is adapted to dry the sampled gas from water molecules while essentially maintaining the composition and properties of other components which are essential for the analysis. According to some embodiments, the polymer substance may also be adapted to wet a gas. For example, in a case of a tube or a membrane, on one side of the tube or membrane the gas is dried, and on the other side the gas is wetted.

According to some embodiments, the polymer substance may exhibit permeability for a fluid that is dependent on the polarity of the fluid, wherein the permeability increases with increasing polarity. For example, the polymer substance may exhibit better permeability to water (which is a polar compound) than to $CO_2$, which is an essentially non-polar compound.

According to some embodiments, the term "permeability" may refer to the ability of a material (such as a polymer substance, for example, a membrane or a tube) to transmit (permeate) fluids (such as water and/or water vapors).

According to some embodiments, the term "polarity" may refer to a dipole-dipole intermolecular force between a positively-charged (even a small positive charge) end of a molecule to a negative (even a small negative charge) end of another or the same molecule.

According to some embodiments, the polymer substance may exhibit pervaporation capabilities (such as pervaporation of water and/or water vapors pervaporation).

According to some embodiments of the invention, the term "pervaporation" may refer to a process that includes the transfer of fluid(s) through a membrane (such as the walls of a dryer polymer tube) wherein the fluid(s) enter the non-porous or porous membrane as vapor or liquid and permeate through the membrane as vapor. The fluid(s) may include water, humidity, water vapor or other fluid such as methanol or any other fluid.

The polymer substance, according to some embodiments of the invention, may be used instead of the Nafion® and may also exhibit better (or essentially similar) water pervaporation performance than the Nafion®. Better water pervaporation may include a faster transfer of water through the material, at selected operating parameters.

According to some embodiments, (dryer) polymer substances used for gas drying (or wetting) purposes should be adapted to allow pervaporation of fluids (such as water and/or water vapors) but also to substantially maintain acceptable mechanical properties (such as strength and flexibility). According to some embodiments, the polymer substance may be adapted to substantially maintain one or more of its initial dimensions (for example, its dimensions prior their use in pervaporation). According to other embodiments, the polymer substance may be adapted to change one or more of its initial dimensions. For example, one or more of the dimensions of a polymer substance may change (for example, grow) during or after its use in pervaporation of fluids. For example, the thickness and/or the length of a membrane and/or a tube may grow when fluid(s) are passed through.

According to some embodiments, the polymer substance may be adapted to be robust in active environments, such as in breath sampling tubes, through which the patient may exhale or inhale medications or other active materials.

According to some embodiments, there are provided three main types of polymer substance, such as the polymer substance membranes or tubes, which are prepared by three main routes: The "grafting (dense) route", the "blend (dense) route" and the "porous route". According to some embodiments, the polymer substances provided herein, are adapted to be easily manufactured and handled, resistant, structurally stable, and/or easily integrated into the desired systems such as membrane systems or tubing systems.

A) Dryer Polymer Substance—the "Grafting (Dense) Route"

According to some embodiments, there is provided a dryer polymer substance, such as, but not limited to, a membrane or a tube, comprising a polymer grafted with a compound having group(s), such as aromatic group(s), for example, phenyl group(s), which group(s) is (are) capable of being sulfonated.

An example of such a group may include styrene or any derivative thereof. According to some embodiments, the dryer polymer substances may also include any material that is adapted to produce selective water (vapor or liquid) transport, particularly, but not limited to sulfonic group type groups (or any derivative or salt thereof). An example of such dryer polymer substance is poly(vinylidene fluoride)-graft-poly(styrene sulfonated acid) (PVDF-g-PSSA) copolymer.

The term "aromatic group" may include, according to some embodiments, conjugated ring(s) of unsaturated bonds, lone electron pairs, and/or empty orbitals exhibiting a stabilization stronger than would be expected by the stabilization of conjugation alone.

The term "sulfonic group" may include, according to some embodiments, any group, compound (such as an anion) having a sulfonic acid residue ($-S(=O)_2-OH$) or any salt (such as $R-S(=O)_2-ONa$) or derivative thereof.

The term "phenyl group(s)" (may also be referred to as a phenyl ring or as -Ph) may include, according to some embodiments, any group of atoms having the formula $-C_6H_5$ or any derivative thereof. According to some embodiments, the term "phenyl group(s)" may cover unsubstituted or substituted phenyl group(s).

The term "styrene" (may also be referred to as vinyl benzene, cinnamene, styrol, ethenylbenzene, phenethylene, phenylethene, as well as other names), is an organic compound with the chemical formula $C_6H_5CH=CH_2$.

The term "polymer" may include, according to some embodiments, any molecule composed of repeating structural units connected to each other, typically, by covalent chemical bonds. The term "polymer" may include, according to some embodiments, a homopolymer (which is a polymer derived from one monomer species), a copolymer (which is a polymer derived from two (or more) monomeric species) or a combination thereof. A polymer, as referred to herein, may include a mixture of polymers. A polymer, as referred to herein, may include linear and/branched polymers which consist of a single main chain with one or more polymeric side chains.

The terms "grafted" or "grafting" may include, according to some embodiments, bonding (for example covalently bonding) to a polymer or a co-polymer, a compound (such as a monomer compound) to produce a polymer or a co-polymer containing bonded compounds (a grafted polymer). An example of a grafted polymer may include a polymer grafted with side chains that has a different composition or configuration than the main chain of the polymer. A more specific example of grafting may include a process wherein styrene monomers are introduced and bonded to a polymer (such as poly vinylidene fluoride (PVDF)) to produce poly(vinylidene fluoride)-graft-polystyrene (PVDF-g-PS) copolymer.

A copolymer, as referred to herein, may include an alternating copolymer, a periodic copolymer, a random copolymer, a block copolymer or any combination thereof.

The term "dryer polymer substance" may include, according to some embodiments, any substance, including but not limited to, a tube or a membrane, that comprises at least one polymer, wherein the substance is adapted to perform pervaporation.

Examples of polymers may include polyolefins (such as polypropylene, polyethylene and copolymers thereof) and/or fluoro-polymers, for example, poly vinylidene fluoride (PVDF) or any other fluoro-polymer such as those which may be found in http://solutions.3m.com/wps/portal/3M/en_US/dyneon_fluoropolymers/Home/Products_and_Solutions/Products/Fluoroplastics/PVDF, which is incorporated herein by reference.

PVDF may include PVDF (homopolymer) and PVDF (copolymer). PVDF (homopolymer) may include poly(vinylidenfluoride) of 1,1-fluoro-ethene. The chemical structure of PVDF (homopolymer) is $-[CF_2-CH_2]_n-$, wherein n is an integer greater than 1.

PVDF (copolymer) may include HFP (hexafluoropropylene)-PVDF copolymer having a chemical structure of $-[CF_2-CH_2]_x-[CF_2-CF(CF_3)]_y-$ wherein x and y are, independently, integers.

The nature and characteristics of the polymer (such as PVDF) being grafted affect the performance and characteristics of a dryer polymer substance. For example, the percentage of grafting of a polymer (such as polyvinylidene fluoride (PVDF) with styrene related compound, or any other suitable compound) may be affected by the degree of crystallinity of the polymer. For example, for a polymer having a lower degree of crystallinity (such as PVDF copolymer), grafting may easily be performed compared to a polymer having a higher degree of crystallinity (such as PVDF homopolymer). The degree of grafting (such as styrene grafting, which may also be referred to as styrenization) of a polymer is related to the amount of the sulfonic acid groups (or any derivative or salt thereof) that can be bound to the grafted polymer. The more styrene compounds in the polymer, the more sulfonic acid groups may be bound. The sulfonic acid groups, as mentioned hereinabove, have a high affinity for water and thus determine the pervaporation characteristics of the dryer polymer substance (of course other factors may also influence the pervaporation characteristics of the dryer polymer substance as well). According to some embodiments, the terms "crystalline" may refer to a solid, such as a polymer, having a structural order. Structural order may include molecules arranged in a regular, periodic manner. Crystallinity, the structural order in a solid, may be detected for example, by diffraction techniques. Materials (such as polymers), can include crystalline and amorphous (a solid showing no long-range order of the positions of the atoms/molecules) regions. According to some embodiments, the term "degree of crystallinity" may refer to the fractional amount (by volume or by mass) of crystallinity in a polymer sample. A "crystalline polymer" may include a polymer showing crystallinity, at least in some region(s) thereof.

Different formulations (for example different ratios of homopolymer/copolymer) may be used in order to optimize the degree of crystalinity and thus the degree of grafting, sulfonation and pervaporation performance of the dryer polymer substance. The ratio of homopolymer/copolymer may also affect the mechanical properties and/or ability to undergo extrusion. For example, a polymer substance produced using a mixture containing about 25% homopolymer with 75% copolymer will exhibit a moderate degree of grafting capability with stiffer structure, compared, for example, to 100% copolymer.

According to some embodiments, grafting (such as styrenization) temperature and styrenization duration also affect the performance and characteristics of the dryer polymer substance.

According to some embodiments, the percentage of grafting (for example styrenization) may be in the range 20-50% (wt), for example, 25-40% (wt), and more specifically 33% (wt). According to some embodiments, the styrenization (grafting) temperature may be in the range of 20° C.-70° C., more specifically, 25° C.-60° C., for example 25° C., 40° C. or 55° C. According to some embodiments, the styrenization includes immersion in 50%-100% styrene (for example 80% styrene in methyl benzene).

After grafting the polymer, sulfonation is being conducted in order to create the pervaporation characteristics of the polymer substance.

The dryer polymer substance may be produced by modification of poly(vinylidene fluoride) (PVDF), for example, PVDF homopolymer, copolymer or both) by irradiation, such as 'gamma' irradiation, followed by chemical treatment of the PVDF infrastructure, incorporating grafts of styrene and then introducing sulfonic acid groups to perform sulfonation of the polystyrene groups. The product of such process is poly(vinylidene fluoride)-graft-poly(styrene sulfonated acid) (PVDF-g-PSSA) copolymer.

Reference is now made to FIG. 1, which illustrates a flowchart 100 describing a general process of production of a dryer polymer substance. Step 110 includes obtaining a polymer (for example, in a solid form, such as powder, particulate or pellet) or a polymer mixture/formulation, for example, PVDF homopolymer, copolymer or a combination thereof). Step 120 includes processing the polymer, for example, by extrusion or by molding (such as injection molding) to produce the desired structure of polymer substance 130 (for example, a polymer tube or membrane). The polymer formulation and the processing of the polymer eventually determine the level of crystallinity of the polymer substance 130. Step 140 includes the activation of the polymer substance 130 which facilitates the grafting in the following step. Activation, which affects the bulk of the substance, may be performed by irradiation of the polymer substance 130 (for example, tube or membrane) or chemical activation using, for example, peroxides. The irradiation, typically gamma radiation, forms terminals (carbon radicals formed by hydrogen atoms removal) to which styrene groups will be bound in the next step. Step 150 includes grafting of a compound having a group which is adapted to be solfonated. Such compound may be a monomer that includes styrene, wherein the styrene is adapted to be sulfonated. This process, which includes grafting of styrene monomers into the polymer, may also be referred to as styrenization. The styrene monomers bind to the terminals formed in step 140. The grafting step (step 140), such as the styrenization step, is performed at a predetermined temperature or temperature gradient and for a predetermined duration, which, together with the level of crystallinity of the polymer substance 130, determines the level of styrenization. This step also includes the polymerization of the compounds adapted to be sulfonated (such as styrene monomers) to form a polymer (such as polystyrene). Step 160 includes the sulfonation of the compounds adapted to be sulfonated, such as the styrene groups, to produce a dryer polymer substance 170. Flowchart 100 shows a process for producing a dryer polymer substance 170, which may include a dryer tube or membrane. As can be seen in flowchart 100, step 120, which includes processing of the polymer (for example by extrusion or by molding), is conducted prior to the steps of irradiation (step 140), styrenization (step 150) and sulfonation (step 160). It was surprisingly found that conducting the steps of irradiation (step 140), styrenization (step 150) and sulfonation (step 160) prior to processing the polymer (step 120) limits the amount of styrene and sulfonic acid groups that can be added to the polymer. In other words, when styrenization and sulfonation exceed a certain level, processing (for example, extrusion) is very problematic and often impossible. According to some embodiments of the invention, processing the polymer (for example, by extrusion or by molding) is conducted prior to the steps of irradiation (step 140), styrenization (step 150) and sulfonation (step 160). This order may allow increasing the styrene/sulfonic acid percentage in the polymer and thus increasing the pervaporation performance of the dryer polymer substance. Known drying substances, such as Nafion®, are extruded after the styrene sulfonic acid is already present in Teflon® (as copolymer with perfluorovinyl ether sulfonate). This limits the amount of styrene/sulfonic acid that could be present in Nafion®, (as the more perfluorovinyl ether sulfonate groups added the harder it is to process) and thus limit the pervaporation performance thereof. In addition, in the case of Nafion®, performing the extrusion after the styrene sulfonic acid is already present in the copolymer results in a more complicated extrusion process, for example, processing temperatures are high (typically 300° C.) and special equipment is required to avoid damage caused by the "aggressive" Nafion® chemicals. It is noted that processing of the polymers disclosed herein (such as PVDF) is, according to some embodiments, easy and does not require special conditions as in the Nafion® processing. In addition, polymers like PVDF are basic and non-expensive as opposed to the Nafion® materials.

According to some embodiments, when the polymer is processed to produce the desired structure of the polymer substance (such as a tube) by way of molding, several advantages may be accomplished. The molding process may improve the integration of the dryer polymer substance within the desired systems and at the same time also improve the mechanical properties of the substance. For example, one or two connectors, structural support and/or reinforcement elements (such as ribs) or any other feature can be molded with the dryer tube. In addition, by the process of molding, any shape can be formed from the polymer(s) compounds, for example, a breath sampling cannula.

Figure 2:
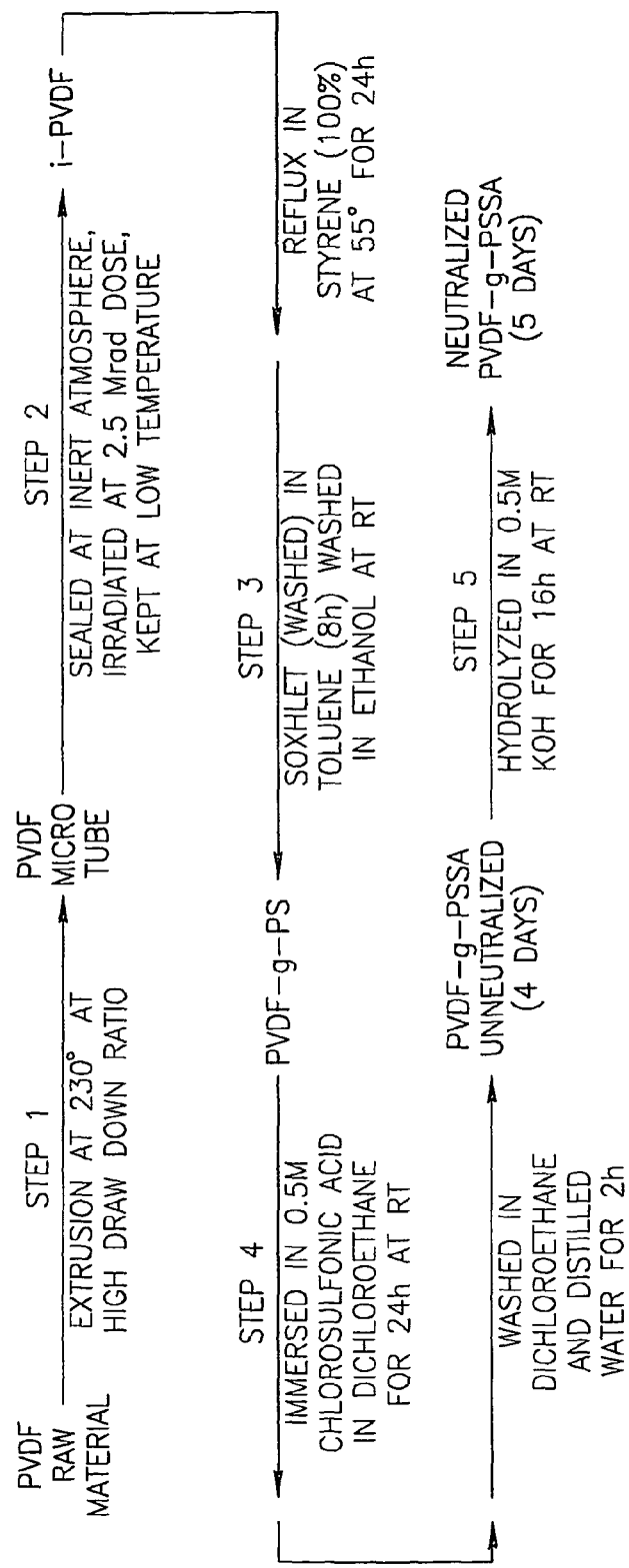
FIG. 2 shows a flow for a process protocol of production of a dryer polymer substance, according to some embodiments.

Reference is now made to FIG. 2, which illustrates a scheme describing an example of a process protocol of production of a dryer tube (including grafting procedure) in a process that may be called a "grafting (dense) route". Step 1 describes obtaining PVDF as raw material and performing an extrusion procedure at 230° C. at a controlled draw down ratio, to produce a PVDF tube (of course, other substances other than a tube, such as membranes, for example, can also be produced in a similar way). In Step 2, the PVDF tube is sealed in an inert atmosphere (such as under nitrogen or helium) and irradiated by gamma radiation at 2.5 Mrad dose at low temperature to produce an irradiated PVDF (i-PVDF) tube. Step 3 describes the incorporation of grafts of polystyrene in the i-PVDF tube. The i-PVDF tube is refluxed in styrene (100%) at 55° C. for 24 hours, washed by Soxhlet in toluene for 8 hours, and then washed in ethanol at room temperature (RT), which is generally 25° C., to produce a PVDF-graft-polystyrene (PVDF-g-PS) tube. Step 4 describes the sulfonation of the polystyrene groups on the PVDF-g-PS tube. The PVDF-g-PS tube is immersed in 0.5 Molar (M) chlorosulfonic acid in dichloroethane for 24 hours at RT, the product is then washed with dichloroethane and distilled water for 2 hours. This step yields an unneutralized poly(vinylidene fluoride)-graft-poly(styrene sulfonated acid (PVDF-g-PSSA) tube, which is then neutralized, in step 5, by hydrolization in 0.5 M KOH for 16 hours at RT.

A comparative study was performed in order to assess the performance of the PVDF-g-PSSA tube and compare it to the performance of the Nafion® tube. The results of this study are summarized in Table 1 below.

TABLE 1

Performance of the PVDF-g-PSSA tubes compared to the performance of the Nafion ® tube.

| Test | Temperature [c.] | RH (relative ambient humidity) [%] | PVDF-g-PSSA tube | Neutralized PVDF-g-PSSA tube | Nafion ® |
|---|---|---|---|---|---|
| Water uptake [%] | 22 | 34 | 261.5 | 395.5 | 22 |
| Leak [μL/min] | 22 | 34 | 10.08 | 10.08 | 10.08 |
| ΔCO$_2$ | 23 | 55 | 1 | 1 | 1 |
| Water evaporation [μL/hour] | 22 | 34 | 292 | 352 | 155 |
| Vapor penetration [μL/hour] | 22 | 34 | No evidence of water in the trap | No evidence of water in the trap | 151 |

For the tubes tested herein: the internal diameter: 1.0±0.1 millimeter (mm); the outer diameter: 1.24±0.02 mm; length 50 mm.

As shown in Table 1, the following five factors were assessed for each type of tube (PVDF-g-PSSA, neutralized (such as Na) PVDF-g-PSSA and Nafion®):

1. Water uptake [%];
2. Leak [micro-liter/minute];
3. ΔCO$_2$ (change in carbon dioxide)
4. Water evaporation [micro-liter/hour]; and
5. Water vapor penetration [micro-liter/hour].

These five factors were tested at the specified temperature [° C.] and relative ambient humidity (RH) [%].

Water uptake measurements were performed by immersing a tube in distilled water at RT for 24 h (or 2 h in boiling water) and checking weight increase [%]. The larger the increase, the more water the tube is capable of absorbing.

Leak measurements were performed by connecting the tube to a differential manometer, creating vacuum in the tube and monitoring the pressure change with time. The results, which are translated into micro-liter/minute, indicate the performance of the tube in blocking gases, such as air, from entering or exiting the tube. As mentioned herein, a tube having good gas blocking characteristics is preferred since it maintains the concentrations of gas elements during measurement.

ΔCO$_2$ measurements were performed by flowing CO$_2$ at a known concentration (for example 5%) through a measurement device with and without a membrane (such as a tube membrane) and comparing the CO$_2$ concentration at the measurement. The difference between the two CO$_2$ concentration readings (with and without the membrane) is indicative of the amount of CO$_2$ that leaked out or "escaped" from the system.

Water evaporation measurements were performed by trapping water in a closed tube and weighing the tube after certain time periods. The decrease in weight is indicative of water evaporation from the tube.

Water vapor penetration measurements were performed by flowing humid gas at 35 ° C. through a tube and trapping the remaining condensed out water (if left) in a trap. The amount of water in the trap is indicative of the amount of water vapor the tube did not absorb/pervaporate. In other words, the more water in the trap, the more water vapor the tube did not absorb/pervaporate.

The following was surprisingly found (as summarized in Table 1):

The PVDF-g-PSSA tubes show significantly better (higher) water uptake than the Nafion® tube.

The PVDF-g-PSSA tubes show better (higher) water evaporation rate than the Nafion® tube.

The PVDF-g-PSSA tubes show better water vapor penetration performance compared to the Nafion® tube (zero evidence to water vapor penetration as opposed to 151 [micro-liter/hour] in the Nafion® tube).

At the same time it was found that the PVDF-g-PSSA tubes do not show any decline in the CO$_2$ barrier properties. In other words, essentially no loss of CO$_2$ from the tube is evident during use, and therefore the PVDF-g-PSSA tubes can be used for CO$_2$ analysis, for example, in breath tests.

As can be seen from Table 1 above, the PVDF-g-PSSA tubes (in its two versions, neutralized and non-neutralized) demonstrate better water pervaporation results than the Nafion® tube. Furthermore, a leak test was carried out continuously every single hour, simultaneous with the vapor penetration test. The leak of the PVDF-g-PSSA tubes was found to stay almost zero, even after 8 hours of the vapor test. In other words, the PVDF-g-PSSA tubes facilitate water pervaporation while at the same time maintain other gas components, such as CO$_2$, and therefore allow reliable gas (such as breath) analysis.

Although neutralized (for example, Na neutralized, such as by use of SO$_3$Na) PVDF-g-PSSA tubes show better water permeability than the non-neutralized PVDF-g-PSSA tubes, both of the two show adequate performances for the gas (for example, breath) dryer tube application. On the other hand, the non-neutralized PVDF-g-PSSA tubes exhibit better mechanical behavior than the Na PVDF-g-PSSA tubes.

Furthermore, under humidity conditions, the PVDF-g-PSSA tubes absorbed certain amounts of water, which in turn improved their mechanical behavior (for example, an increase in flexibility). Considering the superior mechanical behavior and the fact that both types show similar performances in the vapor penetration test, the non-neutralized membrane may be found to be more favorable, according to some embodiments.

One of the key parameters that control the degree of grafting is the degree of crystallinity. The more crystalline the PVDF copolymer is, the less its capability to absorb styrene monomer, which participated in the grafting process. Control of the crystallinity can be done while altering the material formulation with respect to crystallization sensitivity: for example, homopolymer or co-polymer or mixture(s) thereof, and while altering the cooling rate with different cooling medium: for example, water, air, oil and medium temperature. Table 2 below shows the results (including the dimensional stability in the chemical reaction and during the pervaporation action) for PVDF-g-PSSA tubes made from copolymer, homopolymer or mixture(s) thereof. The styrenization reaction took place at 55° C. and also at room temperature (25° C.).

TABLE 2

Performance of differently prepared types of PVDF-g-PSSA tubes compared to the performance of PVC and Nafion ® tubes.

| Test | PVC tube | Nafion ® | PVDF-g-PSSA tube (copolymer at 55° C.) | PVDF-g-PSSA tube (copolymer at 25° C.) | PVDF-g-PSSA tube (homopolymer at 55° C.) | PVDF-g-PSSA tube (homo and copo at 55° C.) | PVDF-g-PSSA tube (homo and copo at 25° C.) |
|---|---|---|---|---|---|---|---|
| Degree of grafting [%] | — | — | 132 | 60 | 30 | 35 | 28 |
| Water uptake [%] | — | 22 | 260 | 60 | 15 | 65 | 22 |
| Leak [μL/min] | 0 | 0-10 | 0-10 | 10-0 | 0-10 | 0-10 | 0-10 |
| $\Delta CO_2$ | — | 1 | 1 | 1 | 1 | 1 | 1 |
| Water evaporation [μL/hour] | — | 155 | 260 | 230 | 43 | 155 | 102 |
| Vapor penetration [μL/hour] (the Δ from PVC) | 433 (0) | 151 (282) | No evidence of water in the trap | 145 (288) | 305 (128) | 159 (274) | 194 (239) |
| Change in thickness due to chemical reaction [%] | — | — | 146 | 60 | 6 | 45 | 12.5 |
| Change in diameter due to chemical reaction [%] | — | — | 97 | 60 | 9 | 37 | 15 |
| Change in thickness due to pervaporation action [%] | — | — | 42 | 36 | 3 | 25 | 11 |
| Change in diameter due to pervaporation action [%] | — | — | 15 | 14 | 3 | 13 | 10 |

Table 3 summarizes experimental results for a polyvinyl chloride (PVC) tube and six types of PVDF-g-PSSA tubes:
1. PVDF-g-PSSA copolymer wherein styrenization was conducted at 55° C.;
2. PVDF-g-PSSA copolymer wherein styrenization was conducted at 25° C.;
3. PVDF-g-PSSA homopolymer wherein styrenization was conducted at 55° C.;
4. PVDF-g-PSSA homo and copolymer wherein styrenization was conducted at 55° C.;
5. PVDF-g-PSSA homo and copolymer wherein styrenization was conducted at 25° C.; and
6. Nafion®.

The following ten factors were assessed:
1. Degree of grafting [%];
2. Water uptake[%];
3. Leak [micro-liter/minute];
4. $\Delta CO_2$ (change in carbon dioxide);
5. Water evaporation [micro-liter/hour];
6. Water vapor penetration [micro-liter/hour] and the Δ (difference) from the PVC measurement;
7. Change in thickness due to chemical reaction (styrenization and sulfonation) [%];
8. Change in diameter due to chemical reaction (styrenization and sulfonation) [%];
9. Change in tube thickness due to pervaporation action [%]; and
10. Change in tube diameter due to pervaporation action [%].

These parameters were measured at a temperature of 23° C. and relative ambient humidity (RH) of 50%.

The following was surprisingly found:

The water uptake of the following tubes was similar to or higher than that of the Nafion®:

PVDF-g-PSSA copolymer wherein styrenization was conducted at 55° C., PVDF-g-PSSA copolymer wherein styrenization was conducted at 25° C., PVDF-g-PSSA homo and copolymer wherein styrenization was conducted at 55° C. and PVDF-g-PSSA homo and copolymer wherein the styrenization was conducted at 25° C.

The water evaporation of the following tubes was similar to or higher than that of the Nafion®:

PVDF-g-PSSA copolymer wherein styrenization was conducted at 55° C., PVDF-g-PSSA copolymer wherein styrenization was conducted at 25° C. and PVDF-g-PSSA homo and copolymer wherein styrenization was conducted at 55° C.

At a lower grafting temperature, such as 25° C., the degree of grafting reached a lower level (which may also results in lower amount of sulfonic groups) compared to the degree of grafting achieved under 55° C. Still, even at a lower grafting temperature, such as 25° C., the performances of the tubes were acceptable for water pervaporation purposes, and in some cases (PVDF-g-PSSA) tube (copolymer at 25° C.) the performances were far better than the Nafion's.

Figure 3:
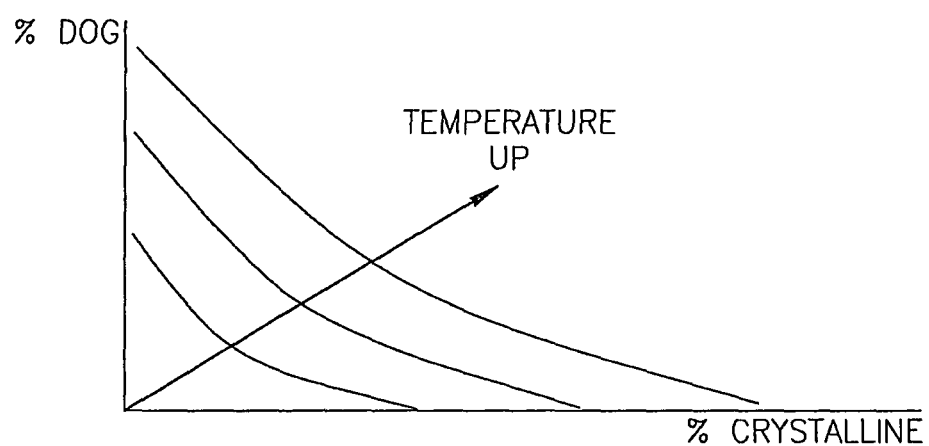
FIG. 3 shows a graph of the effect of temperature and the degree of crystalline (% crystalline) on the degree of grafting (% DOG), according to some embodiments.

In accordance with an additional/alternative embodiment of the invention, there is provided herein a method of monitoring and/or controlling the degree of grafting of polystyrene. This may be accomplished, for example, by adjusting the PVDF material combination between copolymer and homopolymer, changing (for example, reducing) the duration of polystyrene anticipating and grafting process and/or altering/optimizing the cooling procedure during the tube manufacturing in extrusion (for example, Step 1 of FIG. 2). Reference is now made to FIG. 3, which shows a scheme describing how the temperature of the reaction and the degree of crystallinity (% crystalline) may control the degree of grafting (% DOG). The degree of grafting (% DOG) increases with the decrease in the degree of crystallinity (% crystalline). Raising the temperature increases the degree of grafting (% DOG) for a given degree of crystallinity (% crystalline).

Depending on the case and purpose, a specific dryer polymer substance and manufacturing conditions may be chosen. In accordance with an additional/alternative embodiment of the invention, there is provided herein a method for controlling the performance (for example, water uptake, water vapor penetration or any other type of performance) of a PVDF-g-PSSA tube by determining the tube's length.

According to some embodiments, the grafting may be performed in specific areas of the polymer substance, while other areas may remain un-grafted (for example, but not limited to, by blocking arrears of the polymer substance where grafting is not desired). Accordingly, the polymer substances covered under the scope of some embodiments of this invention, may include a polymer substance that comprises grafted areas (for example, grafted with PSSA, and un-grafted areas). This may allow, for example, control of the pervaporation performance of a dryer polymer substance, but may be used for any other application.

Mechanical Properties of Gas Dryer Tubes

Table 3 below shows mechanical properties of PVDF-g-PSSA tube compared to the mechanical properties of a Nafion® tube.

The mechanical properties detailed in the table below were taken from output of tensile test carried out on tube samples with an Instron universal testing machine according to ASTM D638 at a tension rate of 25 mm/min. All values in the table are normalized for purposes of comparison.

TABLE 3 mechanical properties of PVDF-g-PSSA tube compared to the mechanical properties of a Nafion ® tube.

| Tube sample type | Ultimate tensile strength [MPa] | Young's Modulus [MPa] | Ultimate elongation [%] |
|---|---|---|---|
| Nafion ® tube | 20.2 | 152.8 | 81 |
| PVDF-g-PSSA tube (copolymer at 55° C.) | 25.6 | 281.3 | 362 |

The term "ultimate tensile strength" may refer to, according to some embodiments, the stress (the average amount of force exerted per unit area) at which a material breaks or permanently deforms. Tensile strength is a bulk property and, consequently, does not depend on the size (such as length or width) of the test specimen (such as tube). The ultimate tensile strength is normalized to the wall thickness.

The term "Young's modulus" may refer to, according to some embodiments, a measure of the stiffness (the resistance of an elastic body to deformation by an applied force) of an elastic (such as isotropic) material. The Young's modulus is normalized to the wall thickness.

The term "ultimate elongation" may refer to, according to some embodiments, the precentage of stain to rapture.

It can be seen from Table 3 that the PVDF-g-PSSA tube is tougher, stiffer and less brittle compared to the Nafion® tube.

B) Gas Dryer Membrane—the "Blend (Dense) Route"

According to some embodiments, there is provided a dryer polymer substance comprising a hetero-phase polymer composition comprising two or more polymers, wherein at least one of the two or more polymers comprises sulfonic groups, wherein the substance has a permeability for a fluid that is dependent on the polarity of the fluid, wherein the permeability increases with increasing polarity. For example, the polymer substance may exhibit better permeability to water (which is a polar compound) than to $CO_2$, which is an essentially non-polar compound.

The term "hetero-phase polymer" or "hetero-phase polymer composition" may refer to the presence of at least two phases: a continuous or matrix phase and another phase which is a dispersed phase distributed within the matrix phase. The dispersed phase may be discontinuous (such as dispersed islands) or may be a co-continuous phase (such as wherein dispersed islands coalesce into larger islands).

According to some embodiments, the term "co-continuous phase" structure may refer to two or more phases intertwining in such a way that both phases remain substantially continuous throughout at least a portion of the material. The morphology may be analogous to that of a sponge soaked in water where both sponge and water form continuous systems.

According to some embodiments, there is provided a dryer polymer substance, such as, but not limited to, a membrane or a tube, comprising two or more polymers having an essentially hetero-phase structure (for example, a co-continuous phase structure), wherein at least one of the two or more polymers comprising group(s), such as phenyl group(s), which group(s) is (are) capable of being sulfonated. An example of such group may include styrene or any derivative thereof. Such polymers may include, for example, polystyrene (PS) and/or styrene copolymer, such as, styrene-ethylene-butylene-styrene (SEBS) or any derivatives thereof.

According to some embodiments, the dryer polymer substances also include any material that is adapted to produce selective water (vapor or liquid) transport, particularly, but not limited to, sulfonic acid type substances. Examples of such dryer polymer substances are poly(vinylidene fluoride)/polystyrene sulfonated acid (PVDF/PSSA) and poly(vinylidene fluoride)/ styrene-ethylene-butylene-styrene sulfonic acid (PVDF/SEBS-SA). Other polymers which may be used instead of or in addition to the PVDF include polypropylene-homopolymer (PP-homo), polypropylene-random copolymer (PP-raco), medium density polyethylne (MDPE) or any other appropriate polymer. According to some embodiments, at least one of the polymers which form the hetero-phase structure (such as PVDF) create It is noted that the sign "/" (forward slash) between two polymers indicates that the two polymers are adapted to form or are essentially forming a hetero-phase phase structure (such as a co-continuous phase structure). It is distinguished from the sign "g" (graft) between two polymers, which indicates that one of the polymers is grafted in the other polymer.

According to some embodiments, the dryer polymer substances may be produced by physically blending two or more polymers and/or copolymers (such as PVDF with polystyrene (PS) and/or styrene copolymer, such as styrene-ethylene-butylene-styrene (SEBS)) with a compatibilizing agent, followed by the formation of a desired form, such as a tube or a membrane (for example, by extrusion or by molding, such as injection molding) and then sulfonating to produce the dryer polymer substances. This process may be referred to herein as the "blend (dense) route". For example, a poly(vinylidene fluoride)/polystyrene sulfonated acid (PVDF/PSSA) tube may be produced, for example, by:
- a) physically blending PVDF with polystyrene (PS) (or styrene copolymer) with an addition of a unique compatibilizing agent, into an essentially homogeneous blend compound;
- b) producing a tube by extrusion; and
- c) applying a sulfonation process to produce a PVDF/PSSA dryer tube.

The product may then be washed and dried, for example, for one day.

The PVDF and PS are basically non-miscible materials (materials that do not mix to form a homogeneous solution). An attempt to sulfonate a compound of PVDF and PS failed, probably due to this drawback. It was surprisingly found that upon adding a suitable compatibilizing agent (such as, poly (methyl methacrylate) (PMMA) or methyl methacrylate butadiene styrene (MBS)), a PS co-continuous phase was formed and enabled a sulfonation process.

Generally the "blend (dense) route" procedure includes three major steps:
- a) mixing of two or more polymers and/or copolymers (such as PVDF with polystyrene (PS) and/or styrene copolymer such as styrene-ethylene-butylene-styrene (SEBS)) with a compatibilizing agent into an essentially homogeneous blend compound;
- b) processing the polymer mixture to produce a desired form, such as a tube, (for example, by extrusion or by molding, such as injection molding); and
- c) applying a sulfonation process to produce a dryer tube.

Figure 4:
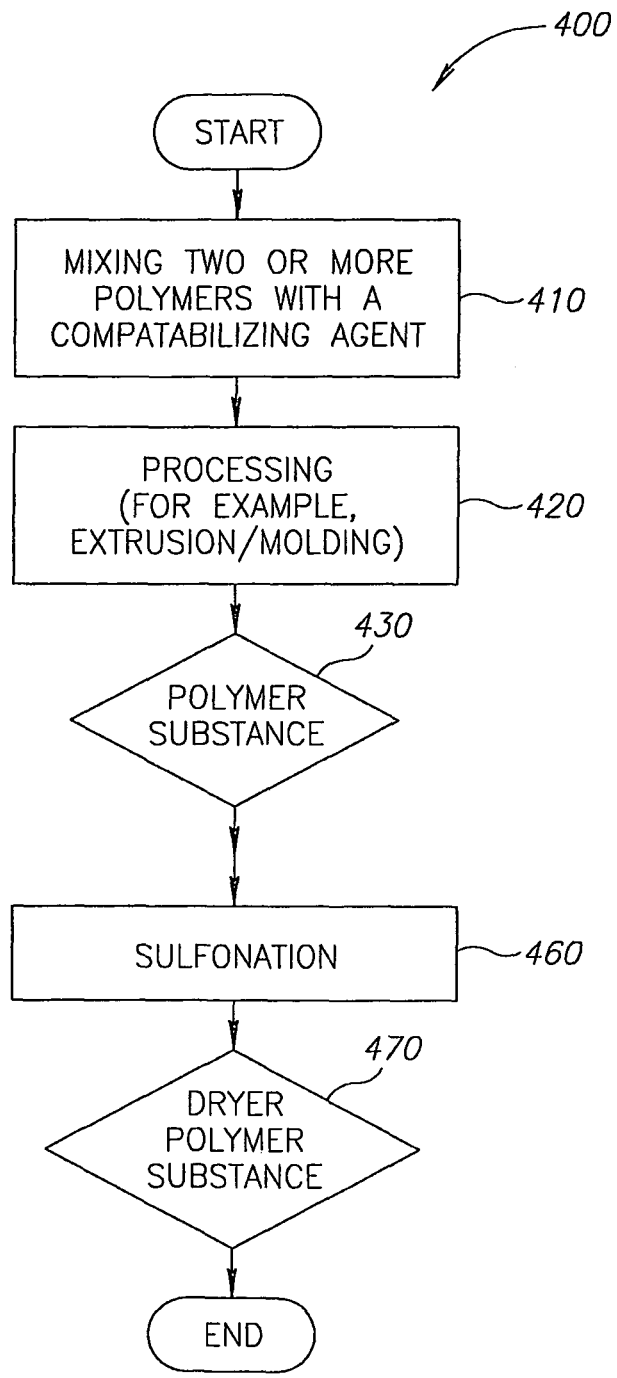
FIG. 4 shows a flowchart describing a general process of production of a dryer polymer substance, according to some embodiments.

Reference is now made to FIG. 4, which illustrates a flowchart 400 describing a general process of production of a dryer polymer substance. Step 410 includes mixing two or more polymers and/or copolymers wherein at least one of the two or more polymers comprises group(s) capable of being sulfonated (for example, mixing PVDF with polystyrene (PS) and/or styrene copolymer such as styrene-ethylene-butylene-styrene (SEBS)) with a compatibilizing agent. The mixture may form into an essentially hetero phase polymer composition (such as a co-continuous phase structure composition). Step 420 includes processing the polymer, for example, by extrusion or by molding (such as injection molding) to produce the desired structure of polymer substance 430 (for example, a polymer tube or membrane). Step 460 includes the sulfonation of the group(s) capable of being sulfonated, such as the styrene groups, to produce a dryer polymer substance 470. Flowchart 400 shows a process for producing a dryer polymer substance 470, which may include a dryer tube or a membrane.

Two types of compounds were developed:
- (a) PVDF/PS/PMMA—70/20/10 (70% PVDF/20% PS/10% PMMA),
- (b) PVDF/SEBS(KRATON)/MBS (PARALOID compatibilizing agent)—49/49/2 (49% PVDF/49% SEBS /2% MBS).

The two compounds (a and b) were found to behave as partial-miscible blends with co-continuous PS phase, which exerted a similar proton exchange function as the PVDF-g-PSSA copolymer mentioned herein. These compounds are easily sulfonated to achieve water vapor pervaporation properties. The sulfonation may be done, for example, by 0.5M of chlorosulfonic acid in di-chloroethane for only one hour.

The results carried out on films made from the compounds a and b are presented in Table 4 below and compared with PVDF and PVDF-g-PSSA films (prior to being converted into a form of pervaporation tubes. The water vapor transmission of PVDF-g-PSSA, 70% PVDF/20% PS/10% PMMA and 49% PVDF/49% SEBS/2% MBS is noticeably better than that of the PVDF.

TABLE 4

Water vapor transmission of different film materials

| Film material | Water vapor transmission [g/A * day] |
|---|---|
| PVDF | 22 |
| PVDF-g-PSSA (copolymer styranization at 55° C.) | 884 |
| 70% PVDF/20% PS/10% PMMA | 1000 |
| 49% PVDF/49% SEBS/2% MBS | 980 |

After proving the feasibility of the blends' membranes (films), tubes were produced from 70% PVDF/20% PS/10% PMMA blend and from 49% PVDF/49% SEBS/2% MBS blend. Both blends were processed in an extruder under the same conditions as the pure copolymer tubes.

Table 5 below shows the performance of the blended tubes, 70% PVDF/20% PS/10% PMMA, 49% PVDF/49% SEBS/ 2% MBS tubes, compared to the performance of PVDF-g-PSSA, Nafion® and PVC tubes.

TABLE 5

Performance of the PVDF-g-PSSA, PVDF/PS/PMMA, PVDF/SEBS/MBS tubes compared to the performance of the Nafion ® and PVC tubes

| Test | PVC tube | Nafion ® | PVDF-g-PSSA tube (copolymer at 55°) | PVDF/PS/PMMA tube | PVDF/SEBS/MBS tube |
|---|---|---|---|---|---|
| Water uptake [%] | — | 22 | 260 | — | — |
| Leak [µL/min] | 0 | 0-10 | 0-10 | 0-10 | 0-10 |
| $\Delta CO_2$ | — | 1 | 1 | 1 | 1 |
| Water evaporation [µL/hour] | — | 155 | 260 | 170 | 211 |
| Vapor penetration [µL/hour] (the Δ from PVC) | 433 | 151 (282) | No evidence of water in the trap | 147 (285) | 125 (308) |

As shown in Table 5, the following five factors (methods are described hereinabove) were assessed for each type of tube (PVDF-g-PSSA, PVDF/PS/PMMA, PVDF/SEBS/ MBS, Nafion® and PVC tubes):
1. Water uptake[%];
2. Leak [micro-liter/minute];
3. $\Delta CO_2$ (change in carbon dioxide)
4. Water evaporation [micro-liter/hour]; and
5. Water vapor penetration [micro-liter/hour].

These parameters were measured at a temperature of 23° C. and relative ambient humidity (RH) of 50%.

It can be seen from the results detailed in Table 5 that the water evaporation performance of both the 70% PVDF/20% PS/10% PMMA and the 49% PVDF/49% SEBS/2% MBS tubes was better that that of the Nafion®. The vapor penetration, and $\Delta CO_2$ performance of the 70% PVDF/20% PS/10% PMMA and the 49% PVDF/49% SEBS/2% MBS tubes were close to that of the Nafion® tube.

It is noted that in the Nafion® case, for example, the viscosity and the processing temperature of the copolymer (Teflon® with perfluorovinyl ether sulfonate) are high (processing temperature about 300° C.). This limits the amount of functional groups (such as sulfonic groups) that can be added to the copolymer (more sulfonic groups will further increase the viscosity and the processing temperature). According to some embodiments of the invention, the processing temperature (such as in step 120 in FIG. 1 and step 420 in FIG. 4) may be significantly less than 300° C., for example in the range of 180° C.-230° C. According to some embodiments of the invention, the sulfonation (for example, step 160 and step 460 in FIG. 4) is being conducted after the processing (for example, step 120 in FIG. 1 and step 420 in FIG. 4) and thus the amount of sulfonation is not limited and can reach approximately 100%.

It is also noted that the copolymer (Teflon® with perfluorovinyl ether sulfonate) used for the preparation of Nafion®, even when neutralized, is very reactive (even aggressive) with the processing equipment (particularly with metals). In contrast, the polymers used to produce the dryer polymer substances, according to embodiments of the invention, are substantially non-reactive with the processing equipment.

Mechanical Properties of Gas Dryer Tubes

Table 6 below shows mechanical properties of PVDF/SEBS/MBS tube compared to the mechanical properties of a Nafion® tube.

The mechanical properties detailed in the table below were taken from output of tensile test carried out on tube samples with an Instron universal testing machine according to ASTM D638 at a tension rate of 25 mm/min. All values in the table are normalized for purposes of comparison.

TABLE 6 mechanical properties of blend (dense) route tube compared to the mechanical properties of a Nafion ® tube.

| Tube sample type | Ultimate tensile strength [MPa] | Young Modulus [MPa] | Ultimate elongation [%] |
|---|---|---|---|
| Nafion ® tube | 20.2 | 152.8 | 81 |
| PVDF/SEBS/MBS 'Dens-blend' tube | 18.5 | 105.6 | 93 |

It can be seen from Table 6 that the mechanical properties of the 'Dens-blend' tube are on the same order of magnitude as those of the Nafion®' tube. As described herein, the mechanical properties of the tube, according to some embodiments, can be improved, for example, by molding support regions, and/or reinforcement element(s) (such as ribs) together with the tube. The support regions may structurally support the tube.

C) Dryer Polymer Substance—the "Porous Route"

According to some embodiments, the present invention provides a robust, high-performance substance (such as a membrane or a tube) designed for the selective removal of a polar fluid, such as water, from less polar gases, such as air and $CO_2$, by a pervaporation process. According to some embodiments, such substance (which can be referred to herein as a dehydration substance or a dryer substance) may include a composite membrane that comprises a support member, generally a support polymer member (such as a support membrane or a support tube) in which is incorporated a cross-linked copolymer that has both positively and negatively charged functionality in a controlled ratio to give the desired selectivity and flux. By changing the ratio of the charged groups and the amount of the copolymer incorporated into the support member, the flux and the selectivity can be controlled for use in specific applications.

It is noted that the terms "membrane" and "tube" may be used interchangeably. It is also noted that the terms "dehydration" and "drying/dryer" may be used interchangeably.

The terms "cross-link" or "cross-linked" may include, according to some embodiments, a branch point from which distinct chains emanate.

Preferred materials for the support polymer (as the support member) that can be used to produce the gas (such as air) dehydration substance include polysulfone (PSU) and polyether sulfone (PES).

In one aspect, the present invention provides a composite membrane including:

(a) a support member that has a plurality of pores (or micro-channels) extending through the support member, and (b) a cross-linked copolymer comprising (i) a cationic monomer and an anionic monomer and/or (ii) a zwitterionic monomer, which cross-linked copolymer fills the pores of the support member, the cross-linked copolymer having a permeability for a fluid that is dependent on the polarity of the fluid, wherein the permeability increases with increasing polarity.

According to some embodiments, the term "anion" or "anionic" may refer to a negatively charged ion.

According to some embodiments, the term "canion" or "canionic" may refer to a positively charged ion.

According to some embodiments, the term "zwitterion" or "zwitterionic" may refer to a chemical compound capable of carrying both a positive and negative charge simultaneously. The total net charge of the chemical compound may be zero (electrically neutral).

In the composite membrane, according to some embodiments of the invention, the cross-linked copolymer fills the pores of the support member laterally, that is substantially perpendicular to the direction of the flow through the composite membrane. By "fill" is meant that, in use, essentially all fluid that passes through the composite membrane must pass through the cross-linked copolymer. A support member whose pores contain cross-linked copolymer in such an amount that this condition is satisfied is regarded as filled. Provided that the condition is met that the fluid passes through the cross-linked copolymer, it is not necessary that the void volume of the support member be completely occupied by the cross-linked copolymer.

In one preferred embodiment, the air dehydration membrane may be a acrylamido-methyl-propane sulfonate (AMPS)-coated polysulfone hollow fiber membrane, or a poly vinyl alcohol-coated polysulfone membrane, or a poly vinyl alcohol-coated polyether sulfone (PES) membrane.

The air dehydration membranes used in accordance with some embodiments of the present invention achieve the selective removal of water vapor while not significantly altering the relative concentrations of oxygen and nitrogen found in the feed stream.

The cross-linked copolymer provides the separating function of the composite membrane in pervaporation separations, and the cross-linked copolymer typically swells in the presence of a polar solvent such as water. In some embodiments, the cross-linked copolymer is a hydrogel. The support member provides mechanical strength to the cross-linked copolymer, and it impedes the swelling of the cross-linked copolymer when the cross-linked copolymer is swellable.

Preferably, the cross-linked copolymer is anchored within the support member. The term "anchored" is intended to mean that the cross-linked copolymer is held within the pores of the support member, but the term is not necessarily restricted to mean that the cross-linked copolymer is chemically bound to the pores of the support member. The cross-linked copolymer can be held by the physical constraint imposed upon it by enmeshing and intertwining with structural elements of the support member, without actually being chemically grafted to the support member, although in some embodiments, the cross-linked copolymer may become grafted to the surface of the pores of the support member.

The term "cationic/anionic copolymer" when used herein refers to a copolymer prepared with cationic and anionic monomers. By cationic monomer is meant a monomer that has a positive charge or a group that can be ionized to form a positive charge. Similarly, by anionic monomer is meant a monomer that is negatively charged or that has a group that can be ionized to form a negative charge. The performance of the composite membrane is mainly determined by the properties of the copolymer anchored within the pores of the support member. The presence of both anionic and cationic sites in the copolymer leads to an increase in intramolecular interactions within the copolymer, leading to a more compact copolymer structure when the copolymer swells in the presence of a polar fluid. This compact nature helps to increase the selectivity of composite membranes, as it provides a denser copolymer structure through which the fluids must pass. The selectivity of the composite membranes is also enhanced by the presence of the support member, as beyond providing mechanical strength, the support member also restricts the swelling of anchored copolymer, which again increases the density of the copolymer.

The anionic monomers used in accordance with some embodiments of this invention are preferably water soluble, although anionic monomers that display little or no solubility in water can be used. Preferred anionic monomers include unsaturated carboxylic acids or salts or anhydrides thereof, and unsaturated sulfonic acids or salts or anhydrides thereof. Unsaturated anionic monomers may contain one, or more than one, carbon-carbon double bond.

Examples of suitable anionic monomers may include anions comprising a sulfonic group such as a sulfonic acid or a salt thereof, such as 2-acrylamido-2-methyl-1-propane-sulfonic acid, 3-allyloxy-2-hydroxy-1-propanesulfonic acid, 2-methyl-2-propene-1-sulfonic acid, 2-propene-1-sulfonic acid, styrene sulfonic acid, vinylsulfonic acid. Other examples of anionic monomers (which may or may not be used together with anions comprising a sulfonic group) may include, acrylic acid, 2-acetamidoacrylic acid, trans-3-benzoylacrylic acid, 2-bromoacrylic acid, 3-chloroacrylic acid, trans-3-(4-chlorobenzoyl)acrylic acid, 2,3-dichloroacrylic acid, 3,3-dichloroacrylic acid, 3,3-dimethylacrylic acid, furylacrylic acid, methacrylic acid, 2-phenylacrylic acid, trans-3-(3-pyridyl)acrylic acid, trichloroacrylic acid, 2-(trifluoromethyl)acrylic acid, propynoic acid (propiolic acid), phenylpropynoic acid, crotonic acid, isocrotonic acid, 3-bromo-2-butenoic acid, 2-chloro-2-butenoic acid, 3-chloro-2-butenoic acid, 2,3-dibromo-4-oxo-2-butenoic acid, 2,3-dichloro-4-oxo-2-butenoic acid, 2,3-dimethyl-2-butenoic acid, 2-ethyl-2-butenoic acid, trans-2-methyl-2-butenoic acid (tiglic acid), cis-2-methyl-2-butenoic acid (angelic acid), 4-oxo-4-phenyl-2-butenoic acid, 2-phenyl-2-butenoic acid, 4,4,4-trifluoro-3-methyl-2-butenoic acid, 3-butenoic acid, 2-hydroxy-4-phenyl-3-butenoic acid, 2-methyl-3-butenoic acid, 2-butynoic acid (tetrolic acid), 2-pentenoic acid, 4-hydroxy-2-pentenoic acid, 2-methyl-2-pentenoic acid (trans), 4-hydroxy-3-pentenoic acid, 4-pentenoic acid, 2,2-dimethyl-4-pentenoic acid, 3-methyl-4-pentenoic acid, 2,4-pentadienoic acid, 2-pentynoic acid, 4-pentynoic acid, 2-hexenoic acid, 2-ethyl-2-hexenoic acid, 3-hexenoic acid, 2-acetyl-5-hydroxy-3-oxo-4-hexenoic acid (dehyrace- tic acid), 5-hexenoic acid, 2,4-hexadienoic acid (sorbic acid), 1-hexen-1-ylboronic acid, 5-hexynoic acid, shikimic acid, 6-heptenoic acid, 2,6-heptadienoic acid, 6-heptynoic acid, 2-octenoic acid, trans-1-octen-1-ylboronic acid, fumaric acid, bromo-fumaric acid, chloro-fumaric acid, dihydroxyfumaric acid, dimethylfumic acid, fumaric acid monoethyl ester, mesaconic acid, maleic acid, bromomaleic acid, chloromaleic acid, dichloromaleic acid, dihydroxymaleic acid, dibromomaleic acid, maleamic acid, citraconic acid, glutaconic acid, 3-methyl-2-pentenedioic acid, itaconic acid, muconic acid, mucobromic acid, mucochloric acid, acetylenedicarboxylic acid, styrylacetic acid, 3-butene-1,1-dicarboxylic acid, aconitic acid, 3-butene-1,2,3-tricarboxylic acid, 2-acrylamidoglycolic acid, 2-sulfoethyl methacrylate, 3-sulfopropyl acrylate, 3-sulfopropyl methacrylate, 3-vinylbenzoic acid, 4-vinylbenzonic acid, tran-2-(4-chlorophenyl)vinylboronic acid, tran-2-(4-fluorophenyl)vinylboronic acid, tran-2-(4-methylphenyl)vinylboronic acid, 2-vinylphenylboronic acid, 4-vinylphenylboronic acid, vinylphosphonic acid, monoacryloxyethyl phosphate, cinnamic acid, alpha-acetamidocinnamic acid, alpha-bromocinnamic acid, 2-bromocinnamic acid, 3-bromocinnamic acid, 4-bromocinnamic acid, 3-bromo-4-fluorocinnamic acid, 4-bromo-2-fluorocinnamic acid, 5-bromo-2-fluorocinnamic acid, 2-carboxycinnamic acid, 2-chlorocinnamic acid, 3 -chlorocinnamic acid(cis), 4-chlorocinnamic acid(trans), 4-chloro-2-fluorocinnamic acid, trans-2-chloro-6-fluorocinnamic acid, trans-2,4-dichlorocinnamic acid, 3,4-dichlorocinnamic acid, trans-2,4-difluorocinnamic acid, trans-2,5-difluorocinnamic acid, trans-2,6-difluorocinnamic acid, trans-3,4-difluorocinnamic acid, trans-3,5-difluorocinnamic acid, 2,3-dimethoxycinnamic acid, 2,4-dimethoxycinnamic acid, 2,5-dimethoxycinnamic acid, 3,4-dimethoxycinnamic acid, 3,5-dimethoxycinnamic acid (trans), 3,5-dimethoxy-4-hydroxycinnamic acid, 4,5-dimethoxy-2-nitrocinnamic acid, alpha-ethyl-cis-cinnamic acid, alpha-fluorocinnamic acid, 2-fluorocinnamic acid, trans-3-fluorocinnamic acid, 4-fluorocinnamic acid, 4-formylcinnamic acid, 2-hydroxycinnamic acid, 3-hydroxycinnamic acid, 4-hydroxycinnamic acid, 3-hydroxy-4-methoxy-trans-cinnamic acid, 4-hydroxy-3-methoxy-trans-cinnamic acid, 4-isopropyl-trans-cinnamic acid, 2-methoxycinnamic acid, 3-methoxycinnamic acid (trans), 4-methoxycinnamic acid (trans), alpha-methylcinnamic acid, 3,4-(methylenedioxy)cinnamic acid, 4-methyl-3-nitrocinnamic acid, alpha-methyl-3-nitrocinnamic acid, alpha-methyl-4-nitrocinnamic acid, 2-nitrocinnamic acid, 3-nitrocinnamic acid (trans), 4-nitrocinnamic-acid (trans), 2,3,4,5,6-pentafluorocinnamic acid, 2-(trifluoromethyl)cinnamic acid, 3-(trifluoromethyl)cinnamic acid, trans-4-(trifluoromethyl)cinnamic acid, 2,3,4-trifluorocinnamic acid, 3,4,5-trifluorocinnamic acid, 3,4,5-trimethoxycinnamic acid (trans), 2,4,6-trimethylcinnamic acid(cis), and their corresponding anhydride or salt.

The cationic monomers are also preferably water soluble, although cationic monomers that display little or no water solubility can also be used. Cationic monomers can be positively charged, or they can bear groups such as amines that are partially protonated in water to form ammonium groups. Preferred cationic monomers include unsaturated amines and unsaturated ammonium salts. Unsaturated cationic monomers may contain one, or more than one, carbon-carbon double bond.

Examples of suitable cationic monomers may include cations having a an ammonium group ($NH_4^+$) (or a salt or a derivative thereof), such as 4-vinylaniline, 3-(acrylamidopropyl)trimethylammonium salt, (2-(acryloyloxy)ethyl](4-benzoylbenzyl)dimethylammonium salt, [2-(acryloyloxy)ethyl]

trimethylammonium salt, diallyldimethylammonium salt, [3-(methacrylamido)propyl]trimethylammonium salt, [2-(methacryloyloxy)ethyl]trimethylammonium salt, propargyamine chloride, vinylbenzyltrimethylammonium salt. Other examples of cationic monomers (which may or may not be used together with cations having a an ammonium group) may include, allylamine, N-allylaniline, allylcyclohexylamine, allylcyclopentylamine, allylmethylamine, N-acryloyltris(hydroxymethyl)methylamine, N-tert-amyl-1,1-dimethylallylamine, N-tert-amyl-1,1-dimethylpropargylamine, diallylamine, 3,3'-diallyl-oxy-diisopropanolamine, 1,1-diethylpropargylamine, N-ethyl-2-methylallylamine, 3-ethynylaniline, 4-ethynylaniline, 1-ethynylcyclohexylamine, geranylamine, N-methylallylamine, propargyamine, vinylamine, (2-(acryloyloxy)ethyl](4-benzoylbenzyl)dimethylammonium salt, [2-(acryloyloxy)ethyl]trimethylammonium salt, 2-aminoethyl methacrylate hydrochloride, N-(3-aminopropyl)methacrylamide hydrochloride, 2-(N,N-dimethylamino)ethyl acrylate dimethyl salt, 2-(N,N-dimethylamino)ethyl acrylate methyl salt, 2-(N,N-dimethylamino)ethyl methacrylate dimethyl salt, 2-(N,N-dimethylamino)ethyl methacrylate methyl salt, ethyl-3-amino-3-ethoxyacrylate hydrochloride, 4-ethynylpyridine hydrochloride, and N-2-vinyl-pyrrolidinone.

The molar ratio of anionic monomer to cationic monomer in the cross-linked copolymer is preferably in the range of from 95:5 to 5:95, more preferably in the range of from 1:9 to 1:1, and the ratio of anionic monomer to cationic monomer is particularly preferable in the range of 1:9 to 1:3. By changing the mole ratio of anionic monomer to cationic monomer, the performance of the composite membrane can be changed.

The anionic/cationic nature of the copolymer can also be obtained by using zwitterionic monomers to form the cross-linked copolymer. The zwitterionic monomers can bear both anionic and cationic groups, or they can bear groups that can be ionized to form negative and positive charges. Preferred zwitterionic monomers include unsaturated zwitterions or precursors thereof that can be readily converted to zwitterions. Unsaturated zwitterionic monomers may include one, or more than one, carbon-carbon double bond.

Examples of suitable zwitterionic monomers include 4-imidazoleacrylic acid, 4-aminocinnamic acid hydrochloride, 4-(dimethylamino)cinnamic acid, 1-(3-sulfopropyl)-2-vinylpyridinium hydroxide inner salt, 3-sulfopropyldimethyl-3-methacrylamidopropylammonium inner salt, and 5-amino-1,3-cyclohexadiene-1-carboxylic acid hydrochloride. Zwitterionic monomers can also be used in conjunction with an anionic monomer, with a cationic monomer, or with both.

While it is preferable that the support member be hydrophilic to facilitate the introduction of a charged cross-linked copolymer and to facilitate the passage of polar fluids, hydrophobic support members can also be utilized in certain situations, such as when a surfactant or a mixed solvent containing water and an organic solvent which wets the support member are utilized. Materials that are suitable for further hydrophilization to produce a hydrophilic support member include, for example, cellulose acetate (CA), poly(vinylidene floride) (PVDF), polysulfone (PSU), polyether sulfone (PES), Nylon 6, poly(ethylene-co-vinyl alcohol) (EVAL) and poly(acrylonitrile) (PAN). Materials that are suitable for making a hydrophobic support member include, for example, polypropylene, poly(tetrafluoroethylene) (PTFE) and poly(vinylchloride) (PVC).

The average pore diameter of the support member can vary widely. According to some embodiments, the average pore diameter may range from about 0.001 to about 20 microns, for example, from about 0.002 to about 5 microns and particularly from about 0.005 to about 1 microns. The porosity of the support member, which is a measure of the pore volume (also referred to as the void volume), may range, according to some embodiments, from about 25 to about 95%, for example, from about 45 to about 85% and particularly from about 0.60 to about 80%. Composite membranes prepared with support members having less than 25% porosity may have low fluxes, while support members with porosity higher than 95% usually do not provide enough mechanical strength to anchor the copolymer.

The support member used, in accordance with some embodiments may either be a symmetric porous membrane or an asymmetric porous membrane. Microfiltration membranes are suitable as symmetric porous membranes, and they preferably have a thickness of from about 10 to 300 microns, more preferably from about 20 to 150 microns, and particularly from 50 to 120 microns. The thinner the support member, the higher the flux.

The asymmetric support member normally has a multi-layered nature, with a dense layer having smaller pores being supported on a backing layer that has larger pores. Ultrafiltration membranes are suitable for use as asymmetric support members. While these support members are described as having "layers", they only comprise a single continuous phase of a single polymer. The layers represent regions having different physical characteristics but the same chemical characteristics. The asymmetric membranes can also comprise non-woven materials (e.g. polyester) which act as mechanical strengthening materials. For asymmetric support members, the thickness of each layer may not critical, as long as sufficient mechanical rigidity is retained. Therefore, in asymmetric composite membranes, the void volume of the support member may not be fully occupied by the cross-linked copolymer. When the composite membrane in accordance with some embodiments of the invention is prepared with an asymmetric support member, the thickness of the dense layer determines the flux of the membranes. It has been observed that asymmetrically filled composite membranes, such as those obtained using ultrafiltration membranes as the support member, lead to pervaporation membranes having higher fluxes.

Asymmetric composite membranes can also be prepared with symmetric support members, by asymmetrically filling the pores of the support member with the cross-linked copolymer. Such asymmetric composite membranes can be prepared by initiating the cross-linking reaction on a single side of the support member, thus obtaining unequal distribution of cross-linked copolymer through the thickness of the support member.

Production of Cross-Linked Copolymer Within a Support Member.

The production of the cross-linked copolymer within a support member (a composite membrane) may include the following steps, in accordance with some embodiments of the invention:

a. Preparation of the porous support member;
 b. Surface-activation;
 c. Impregnation of monomers solution into the porous support member;
 d. Graft co-polymerization of the monomers; and
 e. Cross-linking.
 a. Preparation of the Porous Support Member:

Polymeric support members may be produced by any method known in the art. Washing the obtained polymeric support member with water or water solutions is performed in order to extract (remove) water-soluble polymers that are present in the pores of the polymeric support member and produce the desired porous support members. This washing or extraction step thus clears the pores from undesired impurities (such as homopolymer).

Surfactant-type chemicals (such as any commercially known chemical surfactants for example, Triton, Tetronic, Pluronic, and Softanol) may also be used to better clear the pores. Other surfactants may be used, for example, low molecular weight surfactants such as sodium dodecyl sulfate (SDS) and sodium dodecylbenzenesulfonate (SDBS). Other conventionally used treating materials may also be used for more efficiently clearing the pores; such materials may include low molecular weight alcohols, such as isopropanol (IPA) and ethanol, and solvents such as Freon (chlorinated hydrocarbons). According to some embodiments, the porous support member may be manufactured for the purpose or commercially available.

b. Surface-Activation:

After producing the porous support member, a step of surface-activation may be required. The surface-activation step affects the surface of the support member and/or the surface of the pores of the porous support member. The surface-activation is adapted to facilitate the adhesion of the polar monomers (such as cation and anion monomers/zwitterion that is later polymerized and cross-linked to form the co-polymer pore "filler") to the pores (more precisely to the surface of the pores) of the porous support member. This step is particularly required when the porous support member is of hydrophobic nature (such as PES). According to some embodiments, the surface-activation step includes oxidation and is adapted to introduce carbonyl groups (which are capable of binding to the monomers) to the polymer porous support member.

When hydrophobic porous support members (such as PES) are used, the surface-activation step may be referred to as hydrophilization (or "wetting") of the porous support member to increase the adhesion of the polar monomers. Hydrophilization may be performed by oxidation. Oxidation may be accomplished by any appropriate reagent such as ammonium persulfate, or any other oxidation agents. Other oxidation methods may include ozone treatment, ultraviolet light irradiation, corona discharge, high-voltage electric discharge, plasma treatment or any other method.

Surfactants (such as those mentioned herein) may also be used in the hydrophilization step to improve the results.

c. Impregnation of Monomers Solution Into the Porous Support Member:

After surface-activating the porous support member, the step of impregnation of the monomers solution into the porous support member is performed. This step includes physically introducing to the porous support member a solution containing the cation and anion monomers/zwitterion solution that will later be polymerized and cross-linked to form the co-polymer pore "filler". This solution may be referred to as a pre-polymerized polymer precursor solution. The solution may also include an electrolyte polymer, a polymerization initiator, a cross-linker or any other appropriate additive.

According to some embodiments, ultrasonic energy may be applied to facilitate impregnation.

Conditions for the impregnation step, such as temperatures and/or times, are selected by considering the form or shape of the porous support member to be treated.

In cases where the porous support member is a tube (a hollow fiber) the impregnation step may be accomplished by using a pump, such as a peristaltic pump, to "force" the solution into the tube and into the pores. Another way to facilitate the penetration of the impregnants into the pores is by cutting the tube to a few centimeters length prior to performing the impregnation.

d. Graft Co-Polymerization of the Monomers:

Once the solution containing the cation and anion monomers/zwitterion (and any other required additives) is physically introduced to the porous support member, the step of graft co-polymerization is performed. This step includes the formation of chemically bonding the monomers to the porous support member and co-polymerizing the monomers to produce a co-polymer, which is chemically bound and anchored in place within the pores of the support membrane.

For example, chemical grafting of a PES porous member can be described as a process consisting of surface-activating of the PES porous member, attaching monomers to the reactive sites followed by (or at the same time) polymerization, whereby polymer branches are formed such that they are attached to the main PES polymer. The chemical grafting may be carried out by the abstraction of a hydrogen atom from the hydroxyl group of PES. PES has active labile hydrogen atoms, which can be surface-activated in the presence of a graft initiator, giving rise to free radicals. The free radicals thus produced in the process initiate graft co-polymerization. The series of reaction steps involved in graft co-polymerization of a porous member may be as follows: The graft initiator ion starts the action and the whole process behaves like an autocatalytic one. A small amount of graft initiator ion (such as 10-100 ppm) may therefore be sufficient to carry out the process of graft co-polymerization. The foregoing reactions may take place in the presence of peroxide, which concurrently regenerates the graft initiator, forming a free radical.

The graft initiator may consist of a metal ions system such as $Fe^{3+}$, $Fe^{2+}$, $Ag^+$, $Co^{2+}$ or $Cu^{2+}$. The peroxide may be chosen from the water-soluble catalysts, such as hydrogen peroxide, urea peroxide, ammonium persulfate, potassium persulfate and/or sodium metabisulfite. The monomers and pre-polymers have side functional groups, which may react between themselves and with additional pre-polymers included into the formulation, forming a graft co-polymer.

The initiation of the co-polymerization may be carried out with water-soluble redox initiator combinations customary for emulsion polymerization.

A redox initiating agent may be formed by a combination of the above-mentioned peroxides and a reducing agent, such as a sulfite, a bisulfite, a thiosulfate, formamidinesulfinic acid, and/or ascorbic acid. For example, polymerizations may be conducted in an aqueous emulsion using ammonium persulfate or ammonium persulfate/sodium sulfite redox initiation.

Other or additional polymerization systems may be applied, such as thermal or UV-based polymerization systems, "living" or controlled polymerization, step-growth polymerization, chain-growth polymerization or any combination thereof, or any other polymerising system.

It is also possible to use generally known regulators for the co-polymerization, for example amines (for example, triethylamine, tripropylamine or tributylamine), halogen compounds (for example, chloroform, carbon tetrachloride or carbon tetrabromide), mercaptans (for example, 1-butanethiol, 1-hexanethiol, 1-dodecanethiol, ethyl disulphide, phenyl disulphide or butyl disulphide), alcohols (for example, ethanol, n-/iso-propanol or n-/iso-/tert-butanol), mercaptosilanes or sulphur silanes).

To reduce the viscosity, it is possible to use solvents, for example, aromatic hydrocarbons (for example, toluene, xylene, and so forth), esters (e.g. ethyl acetate, butyl acetate, amyl acetate, cellosolve acetate, etc.), ketones (for example, methyl ethyl ketone, methyl isobutyl ketone, diisobutyl ketone, and so forth), and so forth. The solvent can be added during the course of the free-radical polymerization. Esters having a branched alcohol radical give polymers having a reduced solution viscosity.

e. Cross-Linking:

The function of cross-linking is to control and modulate flexibility of the cross-linked copolymer. According to some embodiments, the cross-linking of the co-polymer hardens the co-polymer (for example, converts it from liquid to gel form) and prevents it from leaking out of the pores. Cross-linking of the co-polymer within the support member can be conducted after or during the co-polymerization. The cross-linking agents used may be highly reactive, have low volatility and have at least two unsaturated groups to form a three dimensional cross-linked structure with the cationic/anionic copolymer.

While water-soluble cross-linking agents are preferred, cross-linking agents that display little or no solubility in water can also be used. Examples of suitable cross-linkers include 3-(acryloyloxy)-2-hydroxypropyl methacrylate, allyl diglycol carbonate, bis(2-methacryloxyethyl) phosphate, 2,2 -bis (4-methacryloxyphenyl)propane, 2,2-bis[4-(2-acryloxyethoxy)phenyl]propane, 2,2-bis[4-(2-hydroxy-3-methacryloxypropoxy)phenyl]propane, 1,4-butanediol diacrylate, 1,3-butanediol dimethacrylate, 1,4-butanediol dimethacrylate, cinnamyl methacrylate, 2-cinnamoyloxyethyl acrylate, trans-1,4-cyclohexanediol dimethacrylate, 1,10-decanediol dimethacrylate, N,N'-diallylacrylamide, diallyl carbonate, diallyl maleate, diallyl phthalate, diallyl pyrocarbonate, diallyl succinate, 1,3-diallylurea, 1,4-diacryloylpiperazine, diethylene glycol diacrylate, diethylene glycol dimethacrylate, diethylene glycol divinyl ether, 2,2-dimethylpropanediol dimethacrylate, dipropylene glycol dimethacrylate, divinyl glycol, divinyl sebacate, divinylbenzene, N,N'-ethylene bisacrylamide, ethylene glycol diacrylate, ethylene glycol dimethacrylate, 1,6-hexanediol diacrylate, 1,6-hexanediol dimethacrylate, N,N'-hexamethylenebisacrylamide, N,N'-methylenebismethacrylamide, 1,9-nonanediol dimethacrylate, pentaerythritol tetraacrylate, pentaerythritol triacrylate, pentaerythritol triallyl ether, 1,5-pentanediol dimethacrylate, 1,4-phenylene diacrylate, tetraethylene glycol dimethacrylate, triallyl cyanurate, triethylene glycol diacrylate, triethylene glycol dimethacrylate, triethylene glycol divinyl ether, 1,1,1-trimethylolpropane diallyl ether, 1,1,1-trimethylolpropane triacrylate, and 1,1,1-trimethylolpropane trimethacrylate.

The amount of cross-linking agent may be from 0.1% to 25%, for example, from 0.5% to 20%, and particularly from 1.0% to 15%, based on the total molar amount of monomers.

Figure 5:
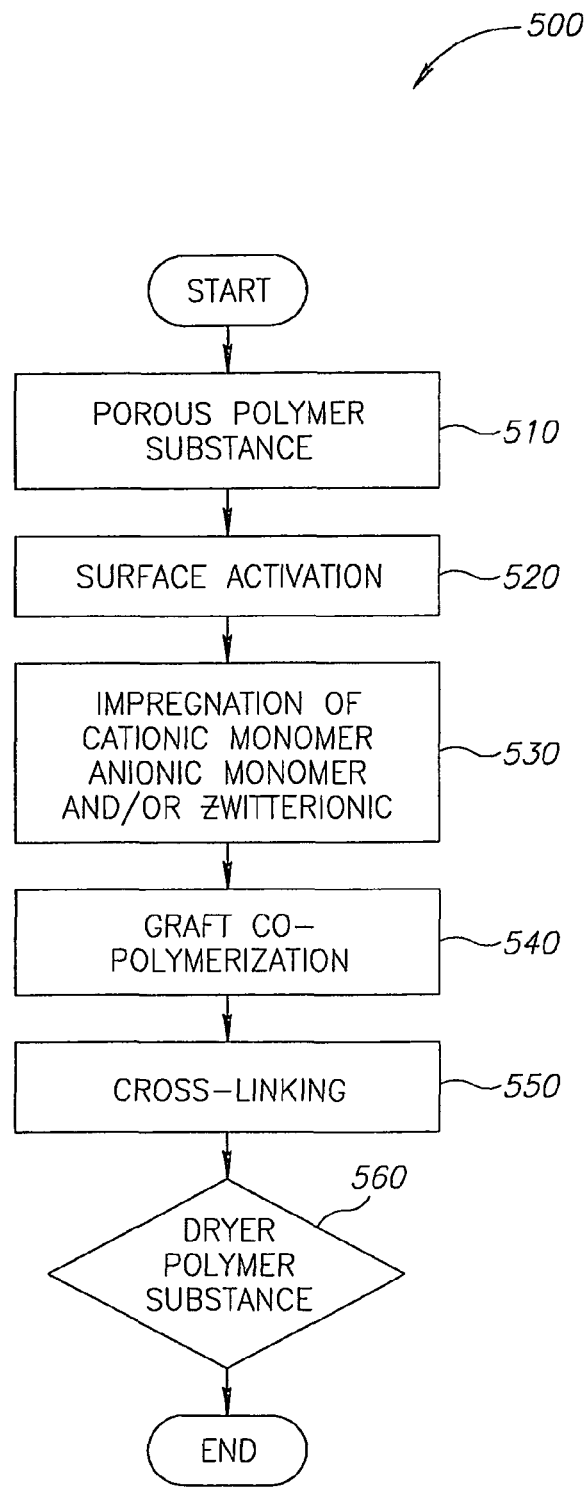
FIG. 5 shows a flowchart describing a general process of production of a dryer polymer substance, according to some embodiments.

Reference is now made to FIG. 5, which shows a flowchart 500 summarizing a general process of production of a dryer polymer substance, according to some embodiments. Step 510 includes obtaining a porous polymer substance (porous support member), for example, a polyether sulfone (PES) porous tube. Polymeric support members may be produced by any method known in the art. This step may include washing the obtained polymeric support member with water or water solutions, performed in order to extract (remove) water-soluble polymers that are present in the pores of the polymeric support member and produce the desired porous support members. Step 520 includes surface-activation of the support member and/or the surface of the pores of the porous support member. The surface-activation is adapted to facilitate the adhesion of the polar monomers (such as cation and anion monomers/zwitterion that is later polymerized and cross-linked to form the co-polymer pore "filler") to the pores (more precisely to the surface of the pores) of the porous support member. Step 530 includes impregnation (introduction) into the porous support member of a solution comprising: (i) a cationic monomer and an anionic monomer, (ii) a zwitterionic monomer, or a combination of (i) and (ii). This step may also be performed, for example, by coating methodologies and/or by impregnation techniques. Step 540 includes graft co-polymerization of the anionic monomer and the cationic monomer and/or the zwitterionic monomer. Step 550 includes cross-linking to form a cross-linked copolymer that at least partially fills the pores of the support member to produce the final dryer polymer substance 560 (a composite membrane/tub) which is adapted to exhibit water pervaporation properties.

EXAMPLES

The following examples are provided to illustrate the invention. It will be understood, however, that the specific details given in each example have been selected for purpose of illustration and are not to be construed as limiting the scope of the invention. Generally, the experiments were conducted under similar conditions unless noted.

In the specific examples that follow, the support member was obtained from the Hydranautics Corporation.

This hollow fiber (support member) is commercially available, and is sold under the trademark HYDRACAP.

The hollow fiber has been used for water purification processes, and is categorized as a UF (ultrafiltration) membrane of Hydranautics Corp. The fiber is made of polyether sulfone (PES), Nominal MWCO, Daltons 150,000. The hollow fiber has an outside diameter of 1.2 mm. The hollow fiber used in these examples is porous and hydrophobic, and has essentially no selectivity between oxygen and nitrogen.

Materials Used for Graft Co-Polymerization

Anionic Monomers Containing Sulphonic Acid Sites:

| AMPS | 2-acrylamido-2-methyl-1-propanesulfonic acid Sodium salt, Lubrisol |
|---|---|
| AMPS 2404 | |
| AMPS 2405 | |
| NaSS | 4-styrene sulfonic acid, sodium salt, Tosoh |

Cationic Monomers Containing Ammonium Sites for Copolymerization:

| APTAC | 3-(acrylamidopropyl)trimethylammonium chloride, Aldrich |
|---|---|
| AETAC | [2-(acryloyloxy)ethyl]trimethylammonium chloride |
| MAETAC | [2-(methacryloyloxy)ethyl]trimethylammonium chloride |
| DMAEA | 2-(N,N-dimethylamino)ethyl acrylate |
| | 4-imidazoleacrylic acid (zwitteronic) |

Polyunsaturated Crosslinking Monomers

| MBAA | N,N'-methylenebismethacrylamide. Aldrich N,N'-bismethylol methylene bisacrylamide |
|---|---|

Free Radical Initiators (Peroxides) Include Inorganic Persulfate, Peroxides, and Redox (APS+NaBS)

| Ammonium persulfate, 98% | ammonium peroxydisulfate, initiator, Aldrich |
|---|---|

-continued

| Sodium metabisulfite, 97% | disodium disulfite and disodium pyrosulfite initiator, Aldrich |
|---|---|
| | hydrogen peroxide |

Free Radical Initiators Include Organic Hydroperoxide and Peroxide; Azo

| Luperox P | Tert-butyl peroxy benzoate, Arkema |
|---|---|
| VAZO 44 | 2,2'-azobis(2-(4,5-dihydroimidazolyl)propane), Du Pont |
| VAZO 56 | 2,2'-azobis(2-methylpropionamidine) dihydrochloride |
| VAZO 68 | 4,4'-azobis(4-cyanovaleric acid) |
| VAZO 88 | 1,1'-azobis(cyclohexanecarbonitrile) |
| AIBN | 2,2'-azobisisobutyronitrile |

Catalyst-Surfactant $SO_3H$ Moieties:

| Cycat 4040 | paratoluene sulfonic acid, catalyst for low temperature reactions |
|---|---|

Monounsaturated Silanes

| MEMO | Methacryloxypropyl-trimethyoxysilane MAPTOS, Evonik |
|---|---|
| VTMO | vinyl-trimethoxysilane |

Polyfunctional Crosslinking Silanes

| TEOS | Tetraethoxyorthosilicate, Evonik |
|---|---|
| GLYMO | Glycidoxypropyl-trimethyoxysilane |
| AMEO | 3-Aminopropyltriethoxy silane |
| DAMO | Gamma-aminopropyl-triethoxysilane |

Example 1

Surface of PES fiber was washed for 30 minutes at RT using 5% ethanol in solution.

Hydrophilization (activation) of the porous support member was performed using ammonium persulfate 0.1%.

After undergoing the above-described treatment, the resultant membrane was cooled to ambient temperature, washed with water for about 10 to about 20 minutes in order to remove the remains of oxidizer, and then dried at about 70° C. for about 40 minutes.

Solution for the impregnation step prepared from cationic monomer was [2-(methacryloxy)ethyl]trimethylammonium chloride (MAETAC), the anionic monomer was sodium salt 2-acrylamido-2-methylpropanesulfonic acid, N,N'-methylenebisacrylamide (MBAA). Their mole ratio was 1000:800:75.

Ammonium persulfate and Na hydrogensulfite were used as the redox initiators, Luperox P was used as free-radical copolymerization initiator—its mole ratio was 0.75:0.04:7.5 on total amount of monomers.

Mixing the above chemicals and diluting them to 50% monomers concentration, stirring the mixture for 0.5-2 hrs until all solids are dissolved in water. The monomer mixture can be added a little at a time or continuously. This allows the evolution of heat to be controlled.

After filtration to remove any undissolved solid by filter paper, the mixture was ready to prepare the membrane. The concentration of the monomers in the solution was 60 wt. %.

The porous membrane was subsequently immersed (impregnated) in a polymer precursor solution comprising of 2-acrylamido-2-methylpropanesulfonic acid, of N,N'-methylenebisacrylamide, radical polymerization initiator, isopropyl alcohol and water, thus filling (impregnating) the membrane with the solution.

Subsequently, the porous substrate was pulled out of the solution. After hollow fiber immersion and removing the excess solution, the membrane was put into an oven at 80° C. (graft co-polymerization), for between 0.5 to 1 hours, until the co-polymerization reaction finished. Cross-linking was performed at 90-110° C.

Example 2

Example 2 illustrates a method for surface-activation of the tubing. Surface of PES fiber is washed to remove some impurities with an appropriate liquid.

Hydrophobic PES membrane is provided with a permanent hydrophilic surface made by depositing a water/alcohol solution for 10 minutes as the impregnation step. Solution 5% ethanol is used to wash the membrane for 30 min at RT.

Once the porous hydrophobic PES membrane was obtained, it was hydrophilized as follows:

A sample of hydrophobic PES membrane (about 6 cm length) was prewetted in isopropyl alcohol (IPA), washed with DI water.

Membrane is immersed in an aqueous solution of oxidizer (ammonium persulfate). The concentration of ammonium persulfate (APS) was about 0.1-3%. The solution was heated from ambient to about 90-95° C. for about 15 minutes. After undergoing the above described treatment, the resultant membrane was cooled to ambient temperature, washed with water for about 10 to about 20 minutes in order to remove the remains of oxidizer and then dried at about 70° C. for about 40 minutes. An impregnation solution was prepared as in Example 1 as well as the steps of impregnation, graft copolymerization and cross-linking.

Example 3

Figure 6:
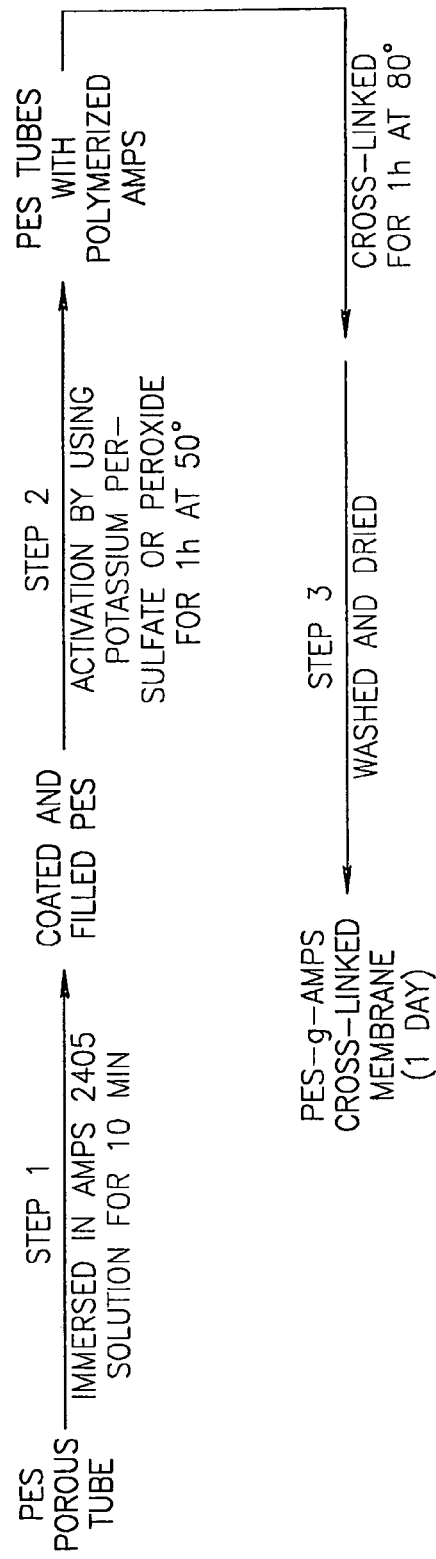
FIG. 6 shows a flow for the process protocol of production of a dryer polymer substance according to some embodiments.

Reference is now made to FIG. 6, which shows a scheme describing an example of a process protocol of production of a dryer tube according to some embodiments. Step 1 includes obtaining a polymeric porous tube, in this case a PES porous tube and coating it with another substance in order to introduce a compound having sulfonic acid moieties into an infrastructure of the porous polymer tube. In this case, coating is performed by immersing the PES porous tube in a solution of acrylamido-methyl-propane sulfonate (AMPS) for 10 minutes to produce a PES tube coated and filled with AMPS. In Step 2, the PES tube, which is coated and filled with AMPS, is surface-activated by using potassium per-sulfate or peroxide for one hour at 50° C. to produce a PES tube having polymerized AMPS. In Step 3, the PES tube having polymerized AMPS is cross linked for 1 hour at 80° C. and washed and dried to produce a PES-g-AMPS cross-linked membrane tube.

Example 4

Table 7 below shows the performance of the porous route tubes, according to some embodiments of the invention, compared with the performance of the Nafion® tube. The first example refers to a PES porous hollow-fiber tube pre-treated with 0.1 wt % of Ammonium per-sulfate oxidizing agent in a surface-activation alcoholic solution, and the second example refers to a PES porous hollow-fiber tube pre-treated with 1.0 wt % of Ammonium per-sulfate oxidizing agent in a surface-activation alcoholic solution.

TABLE 7

Performance of the first and second examples porous route tubes compared to Nafion ® tube.

| Test | Temperature [c.] | RH [%] | First example porous route tubes | Second example porous route tubes | Nafion ® |
|---|---|---|---|---|---|
| Leak [μL/min] | 23 | 55 | 0 | 10.08 | 0 |
| $\Delta CO_2$ | 23 | 55 | 1 | 1 | 0 |
| Water evaporation [μL/hour] | 23 | 55 | 145.2 | 155.4 | 124.8 |
| Vapor penetration [μL/hour] | 22 | 34 | 200 | 100 | 155 |

In the vapor penetration test, a leak test has been taken every hour. The new PES membrane shows stable air leak behavior during the 4-hour test procedure.

As shown in Table 8, the following four factors were assessed for each of the first and second examples of porous route tubes and compared to the Nafion® tube:

1. Leak [micro-liter/minute];
2. $\Delta CO_2$ (change in carbon dioxide)
3. Water evaporation [micro-liter/hour]; and
4. Water vapor penetration [micro-liter/hour].

These four factors were tested at the specified temperature [° C.] and relative ambient humidity (RH) [%].

It was surprisingly found that the water evaporation performance of the first and second examples of porous route tubes was higher than that of Nafion®.

The following is a discussion of the physical mechanisms believed to underlie the operation of the dehydration membranes used herein. However, the invention should not be deemed limited by the following explanation.

It is believed that air and water vapor pass through the dehydration membrane used herein, according to some embodiments, by three different means.

For water vapor penetration, the relevant mechanisms may be:
1) permeation through the dense polymer;
2) viscous flow through the pores; and
3) knudsen flow through the very fine pores.

The permeation through the dense polymer is believed to be the dominant factor for water vapor penetration.

The dryer polymer substance (such as a tube) may be prepared, according to some embodiments, by obtaining a porous polymer tube, cutting into tubes having a desired length (for example, 50 mm) and introducing to the cut porous polymer tubes compound(s) having sulfonic acid moieties (such as in step 520). This may be followed by polymerizing (such as in step 520) and cross-linking (such as in step 520).

The dryer polymer substance (such as a tube) may be prepared, according to alternative or additional embodiments, by obtaining a porous polymer tube, introducing to the tubes compound(s) having sulfonic acid moieties (such as in step 520), polymerizing (such as in step 520) and cross-linking (such as in step 520). The tube may then be cut into tubes having a desired length (for example, 50 mm). Since this order of actions involves treatment of a relatively long tube, there may be a need to use a pump (such as a peristaltic pump) to facilitate the solution penetration into the tube (and/or air, for example, to remove them) and thus improve the homogeneity of the built-up internal coating.

According to some embodiments, part of the treatment (for example, introduction of compound(s) having sulfonic acid moieties) may be performed on a pre-cut tube and another part of the treatment (for example, polymerizing and cross-linking) on a cut tube.

According to some embodiments, the polymer substance may be formed in such ways that allow improving pervaporation, while also improving mechanical properties of the substance. Examples of improved polymer substances and methods of producing same are described in the following paragraphs.

According to some embodiments, coating and/or impregnation and/or grafting of the porous tube may be performed in specific areas of the tube, while other areas may remain un-grafted/uncoated/un-impregnated (for example, but not limited to, by blocking arrears of the porous tube where grafting/coating/impregnation is not desired). Accordingly, the polymer substances (such as a tube) covered under the scope of some embodiments of this invention, may include a polymer substance that comprises impregnated areas (for example, by AMPS and un-impregnated areas). This may allow, for example, control of the pervaporation performance of a dryer polymer substance, but may be used for any other application.

According to some embodiments, the infrastructure of a porous polymer substance (such as a tube or membrane) may be asymmetric, for example, the pores could be larger on one surface of the porous polymer substance (for example, on the outer surface of a tube) and more dense (and/or smaller) on the other surface of the porous polymer substance (for example, inside the tube), Accordingly, the infrastructure of the porous polymer substance can be coated, grafted or impregnated on one surface and not (or less) coated, grafted or impregnated on the other surface. Such a structure can provide, on the one hand, good and fast pervaporation properties (only a thin sulfonated wall to pass through) but much better mechanical strength (the area with the larger pores affect only the mechanical strength of the tube but not the pervaporation).

Another example of an asymmetric porous polymer substance, according to some embodiments, may be a porous polymer tube having larger pores on one or two ends of the tube and more dense pores on the inner part of the tube. The porous tube can thus be coated/grafted or impregnated on the inner part and not (or less) coated/grafted or impregnated on the ends. Such a structure can provide pervaporation properties in the inner part of the tube while the ends of the tube (where no evaporation functionalities are required) may be used to connect to other parts of a tubing system (for example, a breath sampling system).

According to some embodiments, the thickness of a wall of a dryer polymer tube (produced by the "grafting (dense) route", the "blend (dense) route", the "porous route" or by any other method as disclosed herein may be over 130 micrometers, for example over 150 micrometers, in the range of 130-200 micrometers, in the range of 150-300 micrometer, in the range of 200-400 micrometers or over 400 micrometers.

Example 5

Mechanical Properties of Gas Dryer Tubes

The 'Porous-coating' tube cannot be directly compared to the Nafion® tube since its basic matrix is not a continuous morphology, as in the Nafion® and in the blend and grafted types of tubes.

It was established that the 'Porous-coating' tube is more flexible and less prone to kinking and/or collapsing compared to the Nafion® tube.

According to some embodiments, the porous type tube can be made thicker (as the pores are completely filled with pervaporating material) compared to the Nafion® tube. In addition, the pores' size and density can be controlled during the manufacturing of the tube and, therefore, the mechanical properties and pervaporation performance can be optimized.

Exemplary Implementations of Dryer Polymer Tubes

According to some embodiments, the dryer polymer tubes (produced in any process, such as but not limited to, by the "grafting (dense) route", the "blend (dense) route" and the "porous route") may be in various forms and shapes. A certain shape may be selected to affect the mechanical properties (such as strength, kinking or any other property) of the tube as well as the pervaporation capabilities thereof.

Figure 7D:
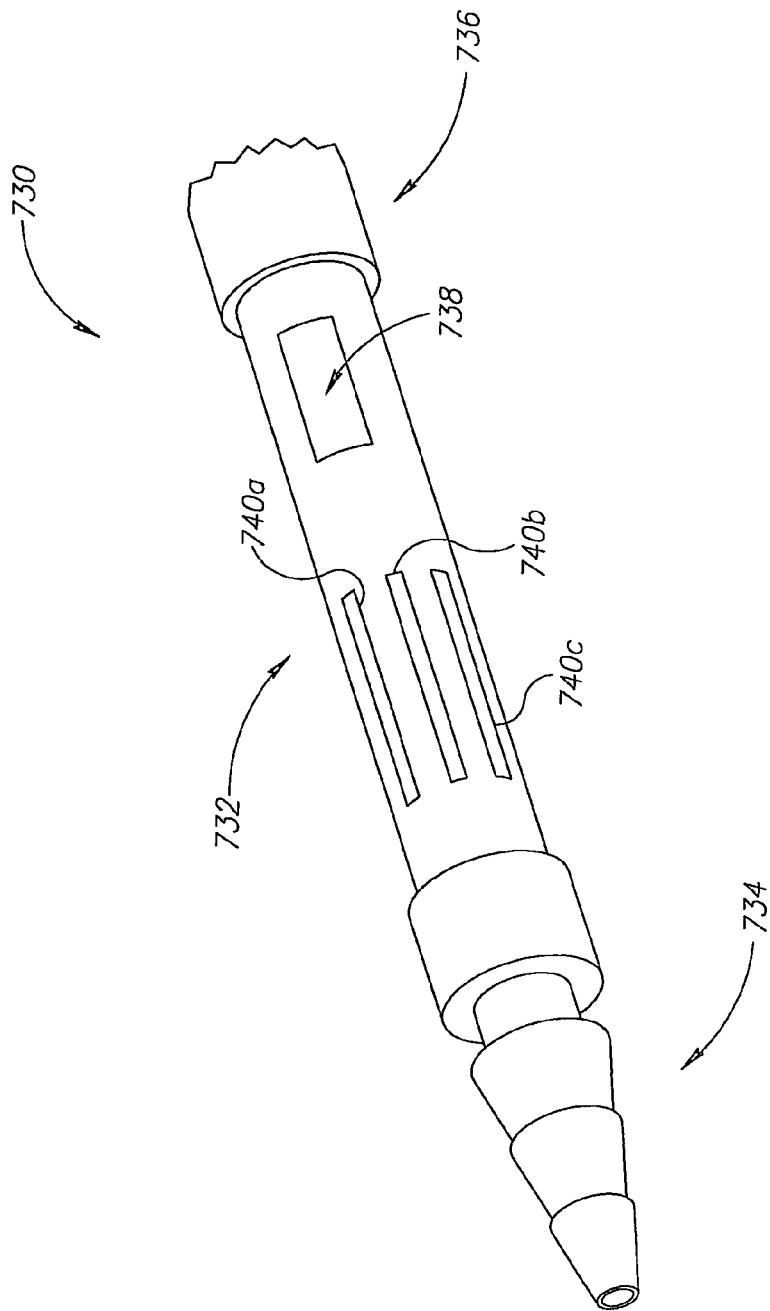

Reference is now made to FIGS. 7a-d, which show exemplary tubes, having different shapes, according to some embodiments. FIG. 7a shows a dryer tube 700 having three areas, end areas 702 and 704 and central area 706. The external diameter of end areas 702 and 704 is d1, and the external diameter of central area 706 is d2. In this case, d1 is larger than d2. The internal diameter d3 of all areas of dryer tube 700 is the same. Such tube may be used for example to allow desired pervaporation performance in central area 706 and structural strength (with or without pervaporation performance) in end areas 702 and 704.

FIG. 7b shows, according to some embodiments, a ribbed dryer tube 710 having, along the length of the tube, an essentially constant internal diameter d4 and two external diameters d5, in the lowered areas 712, and d6 in the elevated areas 714. Elevated areas 714 which extend along the length of the tube may also be referred to as "ribs" which may increase the strength of dryer tube 710. Other types or forms of ribs may also be formed or used. Such ribs may include spiral ribs (not shown), concentric ribs (not shown), or other ribs having any kind of pattern. Tube 710 has an inner conduit 715 adapted to allow a flow of a gas. The internal cross section of the tube is shown to be circular, having a diameter of d4; however, according to some embodiments, the internal cross-section of a tube can also match to an external cross-section of the tube (which may be non-circular) as shown, for example, in FIG. 7c where the internal and external cross-sections have a star shape (will be described in detail hereinbelow). Lowered areas 712 and elevated areas 714 may have similar or different pervaporation performance. These features can be accomplished, for example, by injection molding of the tubes. This cannot be accomplished in Nafion®, which will not maintain its functionality and characteristics in the temperatures and stresses involved in injection molding.

FIG. 7c shows, according to some embodiments, a star-shaped dryer tube 720 having, along the length of the tube, lowered areas 722 and elevated, pointed areas 724. Elevated areas 724 which extend along the length of the tube may increase the strength of dryer tube 720. The internal cross-section 726 of dryer tube 720 matches the external cross-section 728 of dryer tube 720. Lowered areas 722 and elevated, pointed areas 724 may have similar or different pervaporation performance. A non-circular internal cross-section (such as the star-shaped internal cross-section 726 of dryer tube 720, rectangular, square, pointed, flower shaped or any other non-circular internal cross-section) increases the surface area, and the ability to capture liquids in the corners/conduits (formed inside the tube) without blocking the tubing line, and further creating better hydrophillic properties, spreading the fluids (such as water) along the walls of the tube so that they can be easily absorbed and pervaporated.

The internal and/or external cross-section of any dryer tube, may have, according to some embodiments, a circular or a non-circular cross-section, such as, but not limited to, a star-shaped, rectangular, square, pointed, flower shaped or any other non-circular cross-section).

According to some embodiments, the internal and/or external cross-section of any dryer tube may be the same or vary along the length of the tube.

FIG. 7d, shows, according to some embodiments, a dryer tube 730 having a central area 732 and two end areas 734 and 736. Central area 732, which extends between the two end areas 734 and 736, is adapted to pervaporate fluid(s) such as water. According to some embodiments, end areas 734 and/or 736 may be separately formed and assembled with central area 732. According to some embodiments, end areas 734 and/or 736 may be integrally formed with central area 732. In the case where areas 734 and/or 736 are integrally formed with central area 732, dryer tube 730 may be produced according to any method, particularly by molding. According to additional or alternative embodiments, dryer tube 730 (or any other dryer tube according to embodiments of this invention) may include a central area (such as central area 732), which has only defined drying zones (or "windows") such as drying zones 738, 740a, b and c that are adapted to pervaporate fluid(s), wherein the rest of the central area (such as central area 732) is not adapted to pervaporate fluid(s), but rather to provide strength or to "hold" the drying zones. The drying zones (such as drying zones 738, 740a, b and c) may be formed by cutting an area of the central area (such as central area 732) and replacing it with a drying substance (such as a membrane). The drying zones may also be formed by activating/chemically treating/grafting/solfunating and/or applying any other process to certain zones of the central area to convert them into fluid drying zones.

According to some embodiments, in any of the dryer tubes, such as tubes 700, 710, 720 and 730 of FIGS. 7a-d, any process disclosed herein such as grafting, impregnation, activation, surface activation and/or any other process, can be performed on the whole tube or only one or more areas of a tube (such as a central area). The area selective processes may result in a tube having areas with high pervaporation performance and areas with less pervaporation performance but better mechanical properties.

Figure 7E:
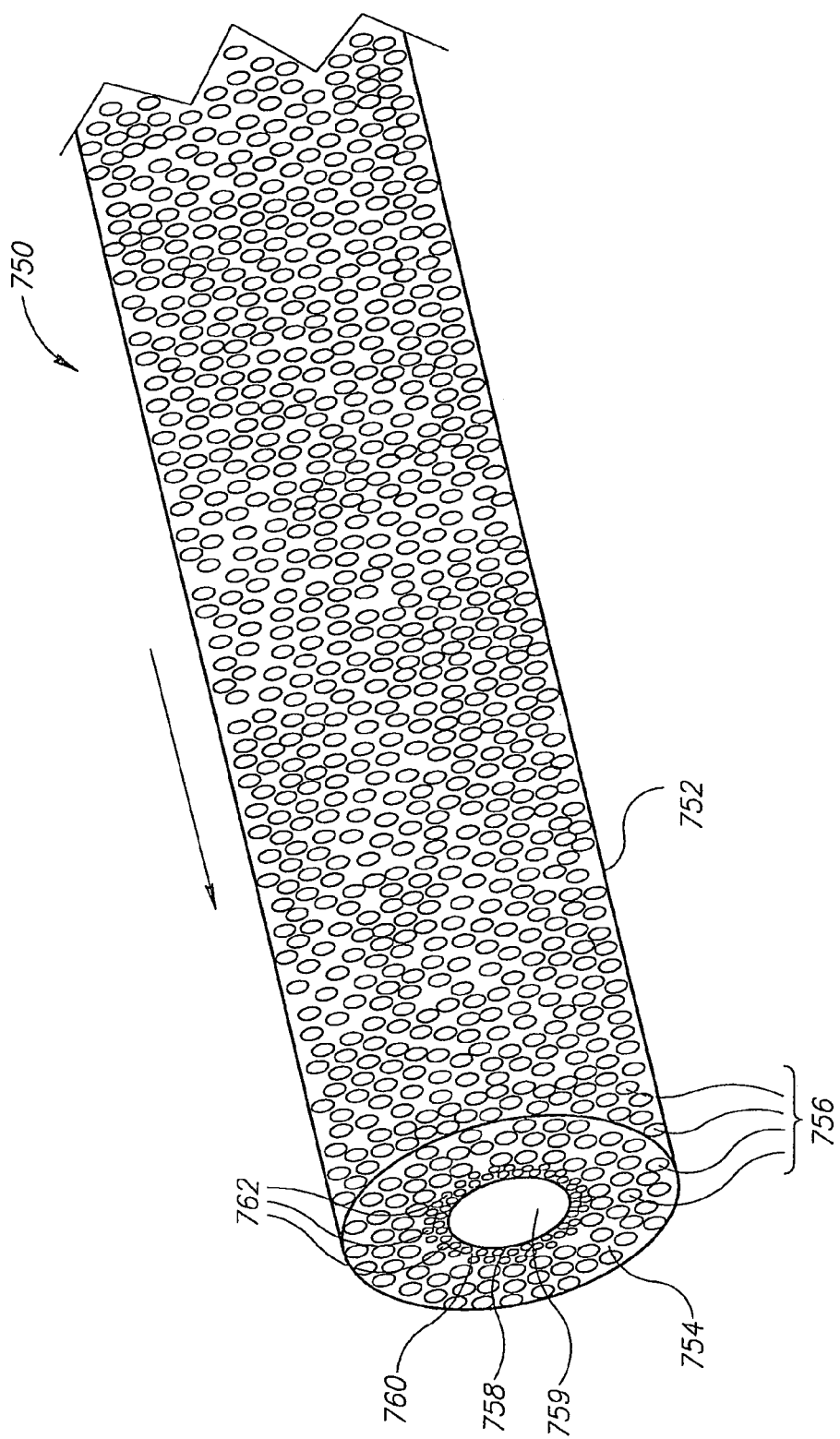
FIG. 7e shows an asymmetric porous dryer tube, according to some embodiments.

Reference is now made to FIG. 7e, which shows an asymmetric porous dryer tube, according to some embodiments of the invention. Porous dryer tube 750 (which may also be described to as a porous support member having pores which may be filled/coated/grafted/impregnated, according to embodiments of the invention) includes an outer surface 752 and an inner surface 758 (defining an inner conduit 759 extending along the length of porous dryer tube 750 and adapted for fluid flow). Dryer tube 750 also includes two sections: a non-dense section 754 and a dense section 760. Non-dense section 754 is located at the area of outer surface 752 and includes large pores 756. Dense section 760 is located at the area of inner surface 758 and includes small pores 762. When fluid flows through inner conduit 759 in the direction of the arrow, water and/or water vapors can pervaporate through the small pores 762 which are adapted to be filled with a cross-linked co-polymer. Once the water and/or water vapors passed the small pores 762 they pass, essentially without interruption, though the unfilled large pores 756 and exit porous dryer tube 750. It is thus possible to obtain a porous dryer tube (such as porous dryer tube 750) having on one hand a relatively thin dense section 760 facilitating efficient pervaporetion and on the other hand a non-dense section 754 which strengthen the tube without affecting the pervaporetion performance.

Figure 8A:
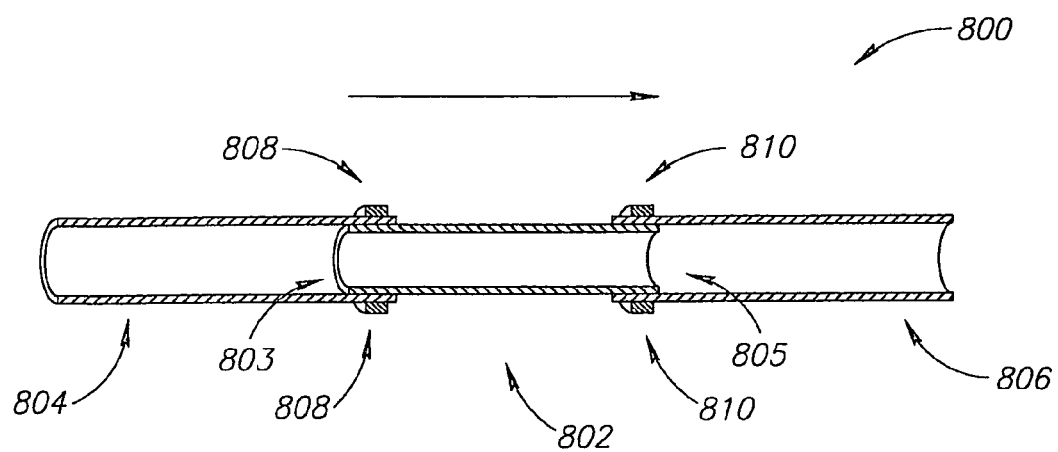
FIGS. 8a-c show longitudinal cross-sections of dryer tubes connected to tubing systems, according to some embodiments.
Figure 8B:
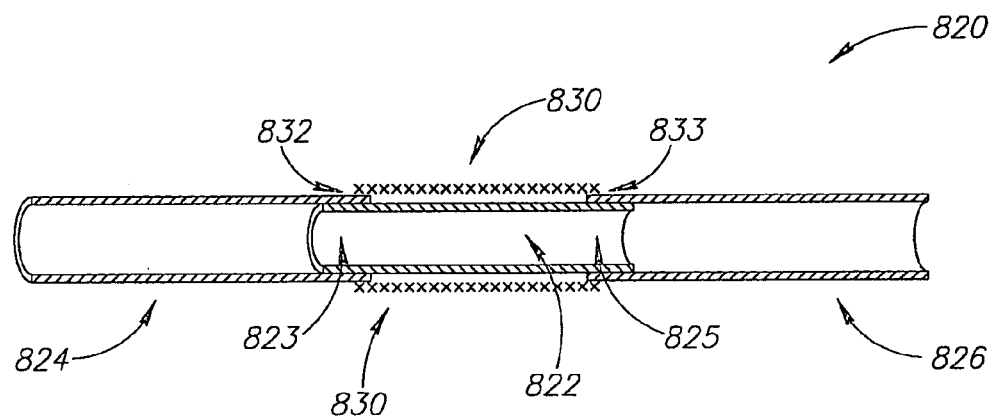
Figure 8C:
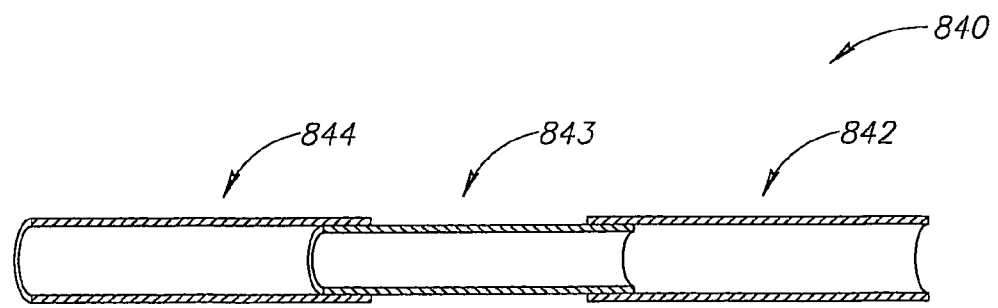

Reference is now made to FIGS. 8a-c, which show dryer tubes connected to tubing systems, according to some embodiments.

FIG. 8a shows a tubing system 800, which includes a dryer tube 802 connected at its first end 803 to a first tube 804 and at its opposing end 805 to a second tube 806. Tube 804 may be used, for example, for collecting breath from a patient to dryer tube 802, and tube 806 may be used, for example, for passing the dried breath from dryer tube 802 to an analyzer. such as a capnograph or any other analyzer that is adapted to provide information related to the patient's breath. The arrow shows the direction of flow in tubing system 800. The external diameter of dryer tube 802 is smaller than the inner diameters of first tube 804 and second tube 806. Thus, first end 803 and opposing end 805 of dryer tube 802 can be inserted into tube 804 and tube 806, respectively. First end 803 and opposing end 805 of dryer tube 802 can be secured to tube 804 and tube 806 by rings 808 and 810, respectively.

FIG. 8b shows a tubing system 820, which includes a dryer tube 822 connected at its first end 823 to a first tube 824 and at its opposing end 825 to a second tube 826. Dryer tube 822, tube 824 and tube 826 may be used, for example, as described in FIG. 8a. The external diameter of dryer tube 822 is smaller than the inner diameters of first tube 824 and second tube 826. Thus, first end 823 and opposing end 825 of dryer tube 822 can be inserted into tube 824 and tube 826, respectively. First end 823 and opposing end 825 of dryer tube 822 can be secured to tube 824 and tube 826 by rings (as shown in FIG. 8a as 808 and 810, respectively). Tubing system 820 also includes a mesh 830, which partially covers the external surface area of dryer tube 822. Mesh 830 also partially covers the external surface area of end area 832 of tube 824 and the external surface area of end area 833 of tube 826. Mesh 830 may function as a protective layer to dryer tube 822, for example, to increase the mechanical strength of the dryer tube 822, if necessary.

FIG. 8c shows a tubing system 840, which includes a dryer tube 842 connected to a tube 844 by a connecting sleeve 843. The external diameter of connecting sleeve 843 is smaller than the inner diameters of dryer tube 842 and tube 844. Dryer tube 842 and tube 844 may be fastened to connecting sleeve 843 for example, by an adhesive, by heating connecting sleeve 843 (particularly if it is made from metal(s)) and thus melting and/or welding dryer tube 842 and/or tube 844, or by an external ring (or clip) as shown in FIG. 8a. A connecting sleeve may also have an internal diameter larger than the external diameter of the dryer tube and another tube and connect them by attaching to the tubes from their outer surface.

What we claim is:

1. A dryer polymer substance comprising a non-porous copolymer grafted with a compound having sulfonic group, said copolymer comprising poly(vinylidene fluoride hexafluoropropylene)-graft-poly(styrene sulfonated acid) (P(VDF-HFP)-g-PSSA) or any derivative thereof, wherein said dryer polymer substance comprises a dryer tube, wherein the percentage of grafting is in a range of 20-50%, wherein the substance is adapted to pervaporate water, water vapor or both from a gas while maintaining the concentration of $CO_2$, $O_2$ or both in said gas, and wherein the tube has a water evaporation rate of over 150 micro-liter/hour at a temperature of 22° C. and at 34% humidity, when the internal diameter of the tube is 1.0±0.1 millimeter (mm); the outer diameter of the tube is 1.24±0.02 mm and the length of the tube is 50 mm.

2. The dryer polymer substance according to claim 1, wherein the percentage of sulfonation of the dryer polymer substance is in the range of 40-100%.

3. The dryer polymer substance according to claim 1, wherein the tube has a water uptake of over 100% at a temperature of 22° C. and at 34% humidity, wherein the internal diameter of the tube is 1.0±0.1 millimeter (mm); the outer diameter of the tube is 1.24±0.02 mm and the length of the tube is 50 mm.

4. The dryer polymer substance according to claim 1, wherein the internal diameter of the tube is 1.0±0.1 millimeter (mm); the outer diameter of the tube is 1.24±0.02 mm and the length of the tube is 50 mm.

5. The dryer polymer substance according to claim 1, wherein said dryer tube has a circular internal cross-section.

6. The dryer polymer substance according to claim 1, wherein said dryer tube has a circular internal cross-section and a non-circular external cross-section.

7. The dryer polymer substance according to claim 1, wherein said dryer tube has a non-circular internal cross-section and a circular external cross-section.

8. The dryer polymer substance according to claim 1, wherein said dryer tube has a non-circular internal cross-section and a matching non-circular external cross-section.

9. The dryer polymer substance according to claim 1, wherein said dryer tube comprises an inner conduit, wherein the internal cross-section of at least a portion of said inner conduit is non-circular and adapted to collect liquids in proximity to the inner walls of said inner conduit and thus allow a liquid free gas flow in said dryer tube.

10. The dryer polymer substance according to claim 9, wherein said cross section of said inner conduit is similar to an n-point star, wherein n is an integer having the value of between 2-10.

11. The dryer polymer substance according to claim 9, wherein said cross section of said inner conduit is similar to an n-petal flower, wherein n is an integer having the value of between 2-10.

12. The dryer polymer substance according to claim 1, having an ultimate tensile strength of about 20 MPa or more as determined by an average amount of force exerted per unit area, when normalized to wall thickness.

13. The dryer polymer substance according to claim 1, having Young's modulus of about 150 MPa or more as determined by a resistance of an elastic body to deformation by an applied force, when normalized to wall thickness.

14. The dryer polymer substance according to claim 1, exhibiting ultimate elongation of 80% or more as determined by a percentage of strain to rapture.

15. A breath sampling system comprising:
A dryer polymer tube comprising a non-porous polymer grafted with a compound having sulfonic groups, said polymer comprising poly(vinylidene fluoride hexafluoropropylene)-graft-poly(styrene sulfonated acid)(P (VDF-HFP)-g-PSSA) or any derivative thereof, wherein the percentage of grafting is in a range of 20-50%, wherein the tube is adapted to pervaporate water, water vapor or both from a gas while maintaining the concentration of $CO_2$, $O_2$ or both in said gas, and wherein the tube has a water evaporation rate of over 150 micro-liter/ hour at a temperature of 22° C. and at 34% humidity, when the internal diameter of the tube is 1.0±0.1 millimeter (mm); the outer diameter of the tube is 1.24±0.02 mm and the length of the tube is 50 mm; and least of:

a connector adapted to connect said dryer polymer tube to a breath sampling tube; and
a reinforcement element.

16. The system according to claim 15, wherein the connector, the reinforcement element, or both, are molded with the dryer polymer tube.

* * * * *